US009103814B2

(12) United States Patent
Ciavarini et al.

(10) Patent No.: US 9,103,814 B2
(45) Date of Patent: Aug. 11, 2015

(54) SOLVENT DELIVERY SYSTEM FOR LIQUID CHROMATOGRAPHY THAT MAINTAINS FLUID INTEGRITY AND PRE-FORMS GRADIENTS

(75) Inventors: Steven J. Ciavarini, Natick, MA (US); Stanley P. Pensak, Jr., East Walpole, MA (US); Jeffrey W. Finch, Gig Harbor, WA (US); Keith Fadgen, Hope Valley, RI (US); Hongji Liu, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 1151 days.

(21) Appl. No.: 12/280,585

(22) PCT Filed: Mar. 16, 2007

(86) PCT No.: PCT/US2007/006679
§ 371 (c)(1),
(2), (4) Date: Nov. 14, 2008

(87) PCT Pub. No.: WO2007/109157
PCT Pub. Date: Sep. 27, 2007

(65) Prior Publication Data
US 2009/0205409 A1    Aug. 20, 2009

Related U.S. Application Data

(60) Provisional application No. 60/783,610, filed on Mar. 17, 2006.

(51) Int. Cl.
*G01N 30/34*    (2006.01)
(52) U.S. Cl.
CPC ..................................... *G01N 30/34* (2013.01)
(58) Field of Classification Search
CPC ....................................................... G01N 30/34

USPC ............... 210/635, 656, 659, 101, 143, 198.2
See application file for complete search history.

(56) References Cited

U.S. PATENT DOCUMENTS 3,981,801 A    9/1976    Knox
4,098,592 A  *  7/1978    Prescott et al. ................... 95/18
(Continued)

FOREIGN PATENT DOCUMENTS

JP    2002 071657 A    3/2002
JP    2003-014718 A    1/2003

OTHER PUBLICATIONS

Machine Language Translation of Japan Patent No. 2002-071657.*
(Continued)

*Primary Examiner* — Ernest G Therkorn
(74) *Attorney, Agent, or Firm* — Locke Lord LLP; Nicholas J. DiCeglie, Jr.

(57) ABSTRACT

A solvent delivery subsystem for a chromatography device performs relatively low pressure, high flow mixing of solvents to form a gradient and subsequent high pressure, low flow delivery of the gradient to the separation column. The mixing of the gradient is independent and does not interfere with the gradient delivery. To form the gradient, the outputs of an aqueous pump and an organic pump are mixed to fill a storage capillary while a downstream point from the storage capillary is vented to atmosphere. After gradient formation, the vent to atmosphere is closed, the solvent delivery system rises to high pressure, and only the aqueous pump runs for gradient delivery. To maintain integrity of the fluid stream, the solvent delivery system uses feed forward compensation and controls at least one parameter selected from the group consisting of pressure and flow in the conduit means to follow a gradual ramp.

16 Claims, 20 Drawing Sheets

(56) References Cited

U.S. PATENT DOCUMENTS

| | | | |
|---|---|---|---|
| 4,767,279 A * | 8/1988 | Dourdeville et al. | 417/18 |
| 4,917,575 A * | 4/1990 | Miller et al. | 417/52 |
| 5,217,590 A | 6/1993 | Lauer et al. | |
| 5,240,603 A * | 8/1993 | Frank et al. | 210/198.2 |
| 5,653,876 A | 8/1997 | Funke | |
| 6,610,201 B2 | 8/2003 | Dourdeville | |
| 6,743,356 B1 * | 6/2004 | Fermier et al. | 210/198.2 |
| 6,780,315 B2 * | 8/2004 | Richardson et al. | 210/198.2 |
| 7,144,502 B2 * | 12/2006 | Fermier et al. | 210/198.2 |
| 7,186,336 B2 * | 3/2007 | Gerhardt et al. | 210/198.2 |
| 2005/0109698 A1* | 5/2005 | Gerhardt et al. | 210/656 |
| 2005/0269264 A1 | 12/2005 | Fermier et al. | |
| 2008/0245136 A1* | 10/2008 | Gerhardt et al. | 73/61.56 |

OTHER PUBLICATIONS

European Search Report for 07 75 3315, dated Aug. 18, 2011, EPO Form 1507S.
International Search Report Issued in PCT/US2007/006679, Dec. 31, 2007, Waters Investment Limited.
Written Opinion Issued in PCT/US2007/006679, Dec. 31, 2007, Waters Investment Limited.
Notice of Rejection in corresponding Japanese Application No. 2009-500516, mailed Sep. 6, 2011.

* cited by examiner

SOLVENT DELIVERY SYSTEM FOR LIQUID CHROMATOGRAPHY THAT MAINTAINS FLUID INTEGRITY AND PRE-FORMS GRADIENTS

CROSS-REFERENCE TO RELATED APPLICATIONS

This application is the U.S. national phase, pursuant to 35 U.S.C. §371, of PCT international application Ser. No. PCT/US2007/006679, filed Mar. 16, 2007, designating the United States and published in English on Sep. 27, 2007 as publication WO 2007/109157 A2, which claims priority to U.S. Provisional Patent Application Ser. No. 60/783,610, filed Mar. 17, 2006. The entire contents of the aforementioned patent applications are incorporated herein by this reference.

BACKGROUND OF THE INVENTION

Liquid chromatography (LC) is an analytical technique in which an analyte or sample is examined. A LC system typically has one or more columns that are packed with a stationary phase material. Generally, the term "column" refers to columns, cartridges, capillaries and the like for performing separations of a chromatographic nature. Columns are typically packed or loaded with a stationary phase. This stationary phase can be particulate or beadlike or a porousmonolith or a substantially inert material. For the purpose of the present disclosure, the term "column" also refers to capillaries which are not packed or loaded with a stationary phase but rely on the surface area of the inner capillary wall to effect separations.

A mobile phase material or solution mixed with the analyte is pumped into the column and the stationary phase material separates and isolates the analyte. The mobile phase material may comprise any fluid, such as, liquids, gases, supercritical fluids or mixtures thereof. Often the analyte elutes directly from the column to an inline detector to generate a chromatogram.

Typically, the analyte is only available in minute quantities so that extreme care must be taken not to waste even the smallest amount. Consequently, LC systems are designed to operate on minute samples or nano-flows with columns that are nano-sized capillaries such as described in U.S. Pat. No. 6,299,767, which is incorporated herein by reference.

Several systems have been developed to accurately and efficiently deliver the mobile phase material or gradient. The delivery of the gradient is often under demanding constraints such as high pressure, e.g., high pressure liquid chromatography (HPLC) systems. For example, U.S. Pat. Nos. 6,858,435 and 6,610,201 describe various techniques in which the solvent composition is formed and delivered. First in, first out (FIFO) is a commonly used technique for forming and delivering the gradient.

Despite the advances noted above, many inherent limitations remain in nano-flow LC systems. Very commonly the gradient is formed for real-time, immediate consumption by the column. As a run may take an hour, this increases the difficulty of maintaining the proper mixture of the gradient under challenging circumstances. In particular, nano-flow LC systems utilize nano-scale flow transducers.

However well-suited to the particular application, nano-scale transducers have a limited dynamic range and are detrimentally subject to thermal effects. Formation of the gradient over a typical period, such as an hour, during which the temperature can fluctuate results in a poor mixture consistency because of the thermal drift of the transducer. Further, on a nano-scale where the transducers may only hold 2 µL of fluid, the high pressure compression of the fluids generates erroneous transducer readings which spoil the mixture. High pressure operation is also at the edge of the tranducer's dynamic range where noise levels can become unacceptable. In short, limited range, noise and thermal drift associated with the transducers are obstacles to meeting the desired performance.

For example, a commercially available nano-flow thermal anemometry type transducer, having a calibration range of 0 to 5 uL/min, operating at an elution flow rate of 250 nL/min, requires repeatable calibration performance of the organic pump down to 7.5 nL/min, for an initial chromatographic starting composition of 3%. This is not an easy performance specification to achieve because the noise level of the device can be as high as +/−5 nL/min, and the thermal sensitivity to noise without thermal compensation can be in excess of +/−4 nL/min per degree Celsius. Thus, a one degree change of the instrument temperature can result in almost a 50% composition error. In an effort to remedy this error, the typical commercially available direct nano-flow LC system employs an external thermal compensation scheme with a temperature sensing element to compensate the flow transducer. Such attempts at compensating for the affects of the thermal sensitivity greatly increase the complexity of the LC system without addressing the underlying problem.

Often, the bulk flow to the LC system is changed during starting and stopping flow, changing flow rates and transitioning flows between operations. During bulk or solvent flow change, it is difficult to maintain the desired composition mixture across the mixing point or node. For example, when the steady-state back pressure of the LC system is very high (e.g., greater than 5,000 psi), the two fluid streams (e.g., solvent and analyte) have significantly different fluid properties (i.e., aqueous and organic solvents) before the mixing node. Due to inherent limitations, such as flow transducers with relatively slow response times (i.e., time constants of several seconds), the necessary feedback is not provided quickly enough to allow the system to be responsive and maintain the desired composition mixture.

Rapid pressure changes from say 10,000 PSI to 200 PSI can cause critical and expensive components like the column to be destroyed. At the very least, the cycles of compression and decompression create apparent flow when none is actually occurring. Also, the compressibility changes of fluid create false readings because the transducers are inherently sensitive to such rapid fluid density changes as the back pressure swings across the typically large range of pressure, and to some extent, the adiabatic heating effect of the fluids. Thus, LC systems that regulate flow between multiple solvent pumps using feed back control cannot maintain accurate measured flow due to the effects of the rapid compressibility changes and heating on the nano-flow transducers.

Another disadvantage of prior art LC systems is cross-flow and back-flow contamination of the flow transducers across the mixing node, which results in contamination of the LC system fluid stream and a temporary loss of flow calibration to the transducers. During rapid decompression or during the normal chromatographic delivery of the gradient, as the viscosity of the fluid drops (i.e., higher organic), prior art LC systems require flow to be reversed back through the mixing node. To buffer the back-flow contamination of the transducers, the connecting conduits between the flow transducers and the mixing node are sized to accommodate the decompression volume of the mixing tee. However, the additional volume becomes lumped with that of the transducers, further exacerbating the rapid compressibility change problems noted above. Thus, conventional high-pressure mixing systems are very susceptible to cross-contamination across the mixing node at very high pressures.

Further, the cross-contamination across the mixing node can create feedback instability between two flow transducers resulting from the fluidic inter-active coupling. The cross-contamination also increases the loss of maximum operating pressure, which is attributed to the large parasitic pressure drops associated with much larger decoupling restrictors required by high-pressure mixing systems to passively stabilize the control interaction. Previous LC systems have recognized these problems and proposed redundant pumps, complex plumbing schemes and valves to isolate the gradient formation pumps from the high-pressure portion of the LC system. Such costly and complex solutions are not only undesirable but the problems remain.

Still further, some LC applications require changing the operational flow rate for a particular choice of column during an injection run, e.g., sample trapping and 2-D chromatography. The flow rate must be started and stopped between selection of each column. Prior art systems have employed some means of valve switching at essentially a no-flow condition to accomplish such flow rate changes. The valve switching components deter from the reliability of the LC system while increasing the expense and complexity in an unfavorable manner.

Other systems have also been developed in an effort to increase the sensitivity and/or collect more data from samples. For example, U.S. Pat. No. 6,858,435 discloses LC analysis systems that make use of a variable flow or peak parking to overcome the difficulty a detector may have in adequately sensing the various species with the sample liquid. When the LC analysis system detects a peak of interest, the LC analysis system controls a micro-switching valve to rapidly reduce the elution flow rate (i.e., reduction in flow by 20 to 50 times). As a result, the elution time of the column-separated compounds is extended to enhance detection. After analysis, the LC analysis system restores the normal elution flow rate. Again, the employment of additional components to accomplish peak parking unfavorably increases the expense and complexity of the system.

Another method to increase the efficiency of LC analysis is to utilize microscale or nanoscale flow rates such as 0.025 to 100 ul/min flow rates. By using such flow rates, the LC analysis system can produce ultra high sensitivity analysis. However, gradient delay and dispersion become problematic. Further, sample loading time and thereby the whole runtime become undesirably long.

As can be seen from the discussion above, closed-loop feedback mechanisms have been developed for LC analysis systems. However, there is a need for still better control and prior art systems do not use feed-forward open-loop mechanisms. Feed-forward is an approach to reacting to changes in a system to minimize or prevent error.

SUMMARY OF THE INVENTION

In view of the above, systems for delivering solvents to chromatography devices that overcome the aforementioned problems of the prior art are needed.

The invention addresses the problems above and others by providing systems and methods for delivering solvents to liquid chromatography devices. The inventors have discovered that by using a feed forward control strategy to compensate the effects of fluid compressibility, with conventional closed-loop feedback control, the ultimate preparation and delivery of the solvent can be greatly improved.

In one embodiment, the subject technology is directed to a system for delivering a gradient to a liquid chromatography device having an injector that introduces the sample into a separations columns. The system includes a first leg having an aqueous pump producing an aqueous output directed through a first inline pressure transducer and a first flow transducer, a second leg having an organic pump producing an organic output directed through a second inline pressure transducer and a second flow transducer and a processing device for controlling the legs. The processing device includes a closed-loop feedback mode to generate a corrective control signal based on a signal derived from at least one of the transducers to overcome parasitic losses upstream from the at least one of the transducers and an open-loop feed forward mode to generate anticipatory control signals based on a parameter of stored energy of the system, wherein the anticipatory control signal calculates a compression flow based on a ratio of compressibility between the aqueous output and the organic output, and wherein the processing device can selectively operate each leg in different modes.

In another embodiment, the subject technology is directed to a fluidic chromatography instrument including a first leg having a pump and transducers for monitoring pressure and flow output from the pump, a second leg having a pump and transducers for monitoring pressure and flow output from the pump, a controller for providing instructions to each pump based on signals from the transducers, and a node for mixing outputs from the first and second legs, wherein the controller can provide a feed forward signal to the first and second pumps based on an ability of the first and second legs to store energy for controlling the compressibility of fluids in the first and second legs to maintain composition control across the node.

In one embodiment, the cycles of compression and recompression are closely controlled by using a feed forward algorithm and/or a linear valve to minimize fluidic disturbances. Further, several components, such as pumps, when used smartly can alleviate needs for additional components.

In another embodiment, an improved system for pre-forming a gradient in a nano-flow solvent delivery system allows efficiently creating and delivering the gradient. Still further, by adding additional components, such as pumps, formerly serial actions can be performed in parallel to reduce elution run and set up time.

Thus, in one aspect, the invention provides a method of forming a gradient for a liquid chromatography system having a pump that fills a storage capillary. The method includes the steps of venting the storage capillary to atmosphere and running the pump at relatively low pressure and higher flow rate to fill the storage capillary until the gradient is formed therein. Preferably, an optimized volume geometry of the storage capillary is sized by a length and an inner diameter to minimize formation of backpressure and gradient dispersion. In another embodiment, the volume capacity of the storage capillary is sized to accommodate the gradient and an overhead of transport volume necessary to move the gradient to a separations column.

The pump may actually be an aqueous pump and an organic pump, each pump having an output connected to a mixing node intermediate the pumps and the storage capillary. During gradient delivery, the organic pump is offline, the vent to atmosphere is closed and the aqueous pump runs to deliver the gradient to a separation column. To purge the storage capillary, the storage capillary is vented to atmosphere and at least one of the pumps is run to ready for forming another gradient.

Formation of the gradient with the storage capillary essentially vented to atmosphere accomplishes three important functions: 1) the formation back pressure is accurately controlled by the geometry of the storage capillary, independent of the column or other connected consumables; 2) the fluid in the storage capillary is purged to waste to prevent upsetting the equilibrium state of the column between injection runs; and 3) any leading or trailing compositional aberrations bracketing the formed gradient, due to starting and stopping the flow during formation, are directed away from the primary fluid stream of the system, i.e., away from the analytical portion and the column therein.

Further, separation of gradient formation at low pressure and isocratic delivery of the gradient at high operational pressures fundamentally eliminates the interdependent coupling of solvent mixture compositional accuracy to changes in flow rate, compared to conventional approaches of high-pressure mixing and delivery. In other words, the subject technology makes gradient formation orthogonal to delivery, which does not change the gradient mixture during the run.

It is a further advantage of the subject technology to provide a solvent delivery system that forms the gradient at high flow rates closer to the transducer's full scale calibration, thereby eliminating the need to extend the dynamic range of the flow transducers far below the elution flow rate, which requires extending the performance at or near the zero-flow calibration of the transducers. By thus avoiding the transducer region that is very susceptible to both noise and thermal drift, the need and additional cost for thermal compensation and characterization of the flow transducer are eliminated while gradient composition accuracy is improved.

Another advantage of the subject technology is the short time intervals to create the gradient, which practically eliminates chromatographic retention time fluctuation due to thermal effects. By forming the gradient in a short time interval, susceptibility to temperature effects is removed. Accordingly, the need for thermal compensation is also reduced or eliminated.

Another advantage of gradient formation at low pressure and subsequent delivery by a single pump is the ease of maintaining the desired composition mixture across the mixing tee.

In another aspect, the invention provides a system for providing a gradient to a nano-flow capillary liquid chromatography device. The system includes an aqueous pump producing a first output, a organic pump producing a second output mixed with the first output to produce a solution and a processing device for controlling the pumps. A storage capillary receives a formed gradient from a portion of the solution. A fitting is connected to the output of the storage capillary, wherein the fitting forms a first outlet connected to the nano-flow capillary liquid chromatography device and a second outlet. A valve connects to the second outlet and is controlled by the processing device such that, during formation of the gradient in the storage capillary, the valve is open to direct resident fluid to waste while the aqueous and organic pumps run.

Preferably, the system also has a first inline pressure transducer and a first flow transducer for receiving the first output and a second inline pressure transducer and a second flow transducer for receiving the second output, wherein each transducer is in communication with the processing device to provide closed-loop feedback control. In one embodiment, the storage capillary, the fitting and the valve are co-located in the thermally managed compartment of the separations column.

Another advantage of the subject technology is to perform gradient delivery by a single pump with the control means of having both a pressure and a flow transducer that allows for very rapid flow changes, return to steady-state flow operation, and elimination of the serious mixture contamination and stability control problems described above. As a result, the subject technology easily accommodates the requirements of performing variable flow or peak parking operation at very high pressures, as compared with conventional high-pressure mixing systems. Further, the need for redundant pumps, complex plumbing schemes and valves in an effort to have the desired isolation of the gradient formation pumps from the high-pressure portion of the system is eliminated.

In another aspect, the invention provides a solvent delivery subsystem for a LC device. The solvent delivery subsystem includes a first pump producing a first output, a first transducer connected to receive the first output for monitoring a parameter thereof, a second pump producing a second output mixed with the first output to produce a solvent mixture, a second transducer connected to receive the second output for monitoring a parameter thereof, a mixing node for combining the first and second outputs and restrictive conduits between each pump and the mixing node to provide passive fluidic decoupling between the first and second pumps to stabilize control interactions across the mixing node. Preferably, the conduits are capillary restrictors and upstream from the first and second transducers.

A further advantage of the subject technology is to prevent cross-flow and back-flow contamination of the flow transducers across the mixing node. Yet a further advantage is to avoid the feedback instability between flow controller. Still a further advantage is to reduce the loss of maximum operating pressure attributed to the large parasitic drops of the larger decoupling restrictors by alleviating the need the for large decoupling restrictors.

Another aspect of the invention provides a system for delivering a gradient to a liquid chromatography device having an injector that introduces the sample into a separations columns. The system includes an aqueous pump producing a first output directed through a first inline pressure transducer and a first flow transducer, a organic pump producing a second output directed through a second inline pressure transducer and a second flow transducer and a processing device for controlling the pumps in a closed-loop feedback mode based on a signal from at least one of the transducers to overcome losses upstream from the transducer.

Preferably, the system has a first fitting for mixing the first and second output to produce a third output and a storage capillary for forming a gradient. The gradient is a portion of the third output. The storage capillary is sized to minimize backpressure and dispersion. A second fitting is connected to the storage capillary, wherein the second fitting forms two outlets, the first outlet being connected to the nano-flow capillary liquid chromatography device. A valve is connected to the second outlet of the second fitting and controlled by the processing device. Upon forming the gradient in the storage capillary, the valve is open to direct resident fluid to waste while the aqueous and organic pumps run. During delivery of the gradient to the nano-flow capillary liquid chromatography device, only the aqueous pump runs and the organic pump is offline.

Still another embodiment of the subject technology is directed to a system for changing an operational flow rate of delivery of a gradient to suit a first column of a nano-flow capillary liquid chromatography device. The system includes a pump producing an output directed through a pressure transducer and a flow transducer, a storage capillary for forming the gradient from a portion of the output and a processing device for controlling the pump and receiving signals from the transducers.

The processing device has a memory storing an instruction set and a processor for running the instruction set. The processor is operative to store a system pressure measurement from the pressure transducer at an end of an injection when a second column of the nano-flow capillary chromatography device is re-equilibrated. The processor is also operative to stop flow to the nano-flow capillary chromatography device, form a new gradient particularly suited to the first column, set a target pressure equal to the system pressure measurement, receive and store a flow rate selected by a user for the first column, and use the pump under closed-loop pressure control with feedback from the pressure transducer to bring a system pressure to the first target pressure. Upon reaching the first target pressure, the processing device transitions the pump to closed-loop flow control with the flow transducer as feedback and the flow rate as a target flow rate to recommence delivery of the new gradient by running the pump.

Preferably, the system also has a second pump producing an output directed through a second pressure transducer and a second flow transducer, a mixing node connected to the storage capillary for combining the outputs of the pumps, and a valve connected to the storage capillary. The valve is controlled by the processor for venting the storage capillary to a pressure below that of an operating pressure of the system.

It is another advantage of the subject technology to accomplish changing the flow rate in a simple, efficient and quick manner without adding to the complexity of the system. Yet another advantage is the ability to overcome the long time constant in trapping applications.

Still another aspect of the invention provides a solvent delivery system for a chromatography device having a short trapping column in series with a restrictive column. The solvent delivery system includes a first pump producing a first output, a pressure transducer and a flow transducer connected to receive the first output. A second pump produces a second output mixed with the first output to produce a solvent mixture. A second pressure transducer and a second flow transducer are connected to receive the second output for monitoring a parameter thereof. A mixing node combines the first and second outputs. A controller operates the pumps with closed-loop feedback. The controller is programmed to use the pressure transducers for the closed-loop feedback in a pressure-control mode, use the flow transducers for the closed-loop feedback in a flow-control mode, use both pumps in the flow-control mode to form a gradient, use only the first pump to deliver the gradient, stop flow by rapidly decompressing the short trapping to column in series with the restrictive column using the pressure-control mode, set a reference pressure set point to zero and commence operation of the first pump to overcome a long time constant of the short trapping column in series with the restrictive column.

In yet another aspect, the invention provides a method for peak parking (sometimes referred to as variable-flow) in a liquid chromatography system including the steps of preforming a gradient from a mixture, controlling a flow rate by using a flow transducer for closed-loop feedback, monitoring a delivery pressure by using a pressure transducer. Based upon a signal to reduce the flow rate based on an elution peak of interest, a target pressure is calculated based on the delivery pressure. The flow rate is controlled by using the pressure transducer as closed-loop feedback with the target pressure as a set point.

Embodiments of the present invention are also directed to methods and apparatus for controlling the composition or maintaining the integrity of a fluid mixture. Differences in the compressibility of compounds forming a mixture may cause the compounds to flow differently. For example, organic compounds are typically more compressible than aqueous solutions. If flow is stopped suddenly in a conduit having a branch containing an organic compound and a branch having an aqueous compound, the branch with the organic compound may experience greater changes in volume associated with pressure changes and may store energy differently. These changes in volume and stored energy results in mixtures that deviate from the desired composition.

One embodiment directed to a device, for use in the context of a fluid stream being conveyed in conduit means under a range of pressure comprising at least one operating pressure and one low pressure and flow rates. The conduit means is in fluid communication with pump means for propelling the fluid under pressure. The conduit means is in fluid communication with valve means, and the valve means has at least a first position and a second position. In the first position the fluid flows in the conduit means, and in the second position fluid does not flow in the conduit means. The device comprises control means and ramp means. The control means is in signal communication with the valve means and in signal communication with ramp means. The ramp means is for controlling at least one parameter selected from the group consisting of pressure and flow in the conduit means. The ramp means performs at least one of the following functions: (i) in response to the placing or anticipated placing of the valve means in the second position, while said conduit means is at said one or more operating pressures, the control means commanding said ramp means to decrease the selected parameter in said conduit means in a first ramp until such low pressure is attained; and (ii) in response to the valve means assuming the first position or in anticipation of the valve means assuming the first position, to increase the selected parameter until the one or more operating pressures is attained in a second ramp.

As used herein, the term "pump means" refers to any means for propelling a fluid. These means comprise serial and parallel pumps, turbine pumps, syringe pumps, peristaltic pumps, electrokinetic pumps, pneumatic amplifiers and fluids propelled through compressed storage devices. The term "fluid communication" refers to fluid connections of a plumbing type. The term "valve means" is used to denote any device capable of interrupting the flow of fluid. Chromatographic instruments have sample injectors that are a special form of a valve.

As used herein, the term "control means" refers to computers, computing processing units (CPUs), micro-controllers, digital signal processors, (DSPs), servers, analog devices programmed with suitable firmware or software. Analytical instruments often have computers and CPUs controlling aspect of the operation. Software to control single instruments and multiple instruments through local or centralized computers are well known in the art. The term "signal communication" refers to electrical connections or circuits, optical connections, wireless communications through radio waves, internet connections, and other means by which equipment may communicate.

Another embodiment of ramp means comprises pump control means. The pump control means can be a separate computer, computing processing unit (CPU), micro-controller, DSPs, server or the same control means controlling other functions. The pump control means is for commanding one or more pumps to place at least one fluid in the conduit means under a pressure in at least one of the first ramp or second ramp. In order to reduce pressure or reduce flow, the pump control means, particularly with small diameter conduit means, may need to reverse in pumping direction.

One embodiment of the present invention features valve means in the form of a valve for controlling flow from a trapping column. Another embodiment of the present invention features valve means in the form of a sample injection means. Sample injection means are known in the art under several names, such as sample managers, autosamplers, sample modules and the like. Sample injection means are a form of a multi-port valve with a loop of conduit in which the sample is placed. With the sample placed in the loop the multi-port valve is placed with the loop in fluid communication with the conduit means in fluid communication with pump means. The sample injection means has a first position and a second position. In the first position, the sample injection means receives a fluid sample at a range of pressure comprising atmospheric pressure to the low pressure. In the second position, the sample injection means is in fluid communication with the conduit means for placing the fluid sample in therein.

One embodiment of the present device has features drawn to the sample injection means. The sample injection means is in fluid control with a pressure source for placing a pressure in the sample means. The pressure source is in signal communication with control means, and control means commands the pressure source to place the sample injection means under atmospheric or an initial pressure for receiving the sample. And, after the sample is received, the control means commands the pressure source to increase pressure to the low pressure corresponding to the pressure in the conduit means.

Preferably, the device further comprises at least one pressure sensor in signal communication with the control means. The pressure sensor is in fluid communication, that is, measures the pressure of at least one of the pump means, conduit means and valve means.

Preferably, the device comprises pump means. One embodiment of the present invention features pump means comprising at least a first pump for a first solvent and a second pump for a second solvent. The conduit means comprises at least one first branch in fluid communication with said first pump and a second branch in fluid communication with said second pump. The first branch and second branch are in fluid communication at a tee fitting wherein said first solvent and second solvent form mixtures which comprise the fluid.

Preferably, one pump is selected from said first and second pump for control ramped to pressure. Preferably, at least one pump is selected for control based on flow. With respect to control ramped to flow, the flow of such pump is preferably controlled to track the flow of the pump ramped to pressure, preferably compensating further for the compressed volume of fluid. That is, the pump tracking flow tracks the flow for the solvent for which is expected to pump as a percentage of the total fluid plus an additional volume of fluid representing the difference between the compressed and uncompressed volume of the solvent. Preferably, the pump ramped to pressure is for an aqueous solvent. And, the pump ramped to flow is for an organic solvent.

And, preferably the device has at least one flow sensor in signal communication with the control means and in fluid communication with pump means, conduit means or valve means. The flow sensors allow the matching of flow. As used herein, flow sensors may also comprise stepped motors which relate to piston movements which can be related to flow.

The device of the present invention features a ramp means which coordinates the opening and closing of valve means with a pressure ramp in the conduit means. The ramp is gradual in the sense that the increase of decrease in pressure is not immediate, having a slope of pressure over time of not greater than approximately 10,000 pounds per square inch (psi) per second. More preferably, the slope is in the range of 10 to 1,000 psi per second, and, more preferably, 100 to 500 psi per second.

A further embodiment of the present invention is drawn to a method of maintaining the integrity of a fluid. The method is for use in the context of a fluid stream being conveyed in conduit means under a range of pressure comprising at least one operating pressure and one low pressure. The conduit means is in fluid communication with pump means for propelling the fluid under pressure. The conduit means is in fluid communication with valve means, and the valve means has at least a first position and a second position. In the first position the fluid flows in the conduit means, and in the second position fluid does not flow in the conduit means. The method comprises the step of controlling at least on parameter selected from the group consisting of pressure and flow in the conduit means. The parameter is controlled in at least one of the following steps:

(i) in response to the placing or anticipated placing of the valve means in the second position, while the conduit means is at said one or more operating pressures, to decrease the selected parameter in the conduit means in a first ramp until the low pressure is attained; (ii) in response to the valve means assuming the first position or in anticipation of the valve assuming the first position while the conduit means is at the low pressure to increase the selected parameter until one or more operating pressures in a second ramp is attained.

Thus, embodiments of the present invention are directed to controlling the composition or maintaining the integrity of a fluid mixture. Differences in the compressibility of compounds forming a mixture may cause the compounds to flow differently. These changes in volume and stored energy results in mixtures that deviate from the desired composition. Embodiments of the present invention gradually reduce the stored energy of the conduits, pumps and valves prior to disrupting the flow. These and other features of the present invention will be apparent from viewing the drawings and studying the text of the Detailed Description that follow.

Another embodiment of the subject technology is directed to a LC instrument including an injection valve for creating a gradient, an analytical column in fluid communication with the injection valve, a pump connected to the injection valve for urging the gradient towards the analytical column and a device intermediate the injection valve and analytical column for storing the gradient.

It should be appreciated that the present invention can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

DETAILED DESCRIPTION OF CERTAIN ILLUSTRATIVE EMBODIMENTS

The present invention overcomes many of the prior art problems associated with delivering solutions to nano-flow capillary LC instruments. The present disclosure maintains the integrity of a fluid mixture by recognizing when undesirable mixing may occur and employing pump settings to prevent such mixing. The present disclosure also illustrates preforming gradients a low pressure and high flow in order to increase throughput of LC instruments. The advantages, and other features of the system disclosed herein, will become more readily apparent to those having ordinary skill in the art from the following detailed description of certain illustrative embodiments taken in conjunction with the drawings which set forth representative embodiments of the present invention.

All relative descriptions herein such as upstream, downstream, left, right, up, and down are with reference to the Figures, and not meant in a limiting sense. Additionally, for clarity, common items such as filters, conduits and interconnections have not been specifically included in the Figures as would be appreciated by those of ordinary skill in the pertinent art. Unless otherwise specified, the illustrated embodiments can be understood as providing exemplary features of varying detail of certain embodiments, and therefore, features, components, modules, elements, subsystems and/or aspects of the illustrations can be otherwise combined, interconnected, sequenced, separated, interchanged, positioned, and/or rearranged without materially departing from the disclosed systems or methods.

Linear Valve Embodiments

Referring to FIGS. 1A-2B, a direct-flow nano-scale HPLC instrument 111 that uses a linear valve 127 in accordance with the subject technology is shown. The linear valve 127 allows the HPLC instrument 111 to efficiently transition between the desired operating pressures. It is envisioned that the HPLC instrument may operate at pressures exceeding 5,000 pounds per square inch (PSI) as recently instruments have been introduced into the marketplace capable of operation at 15,000 PSI.

Figure 1A:
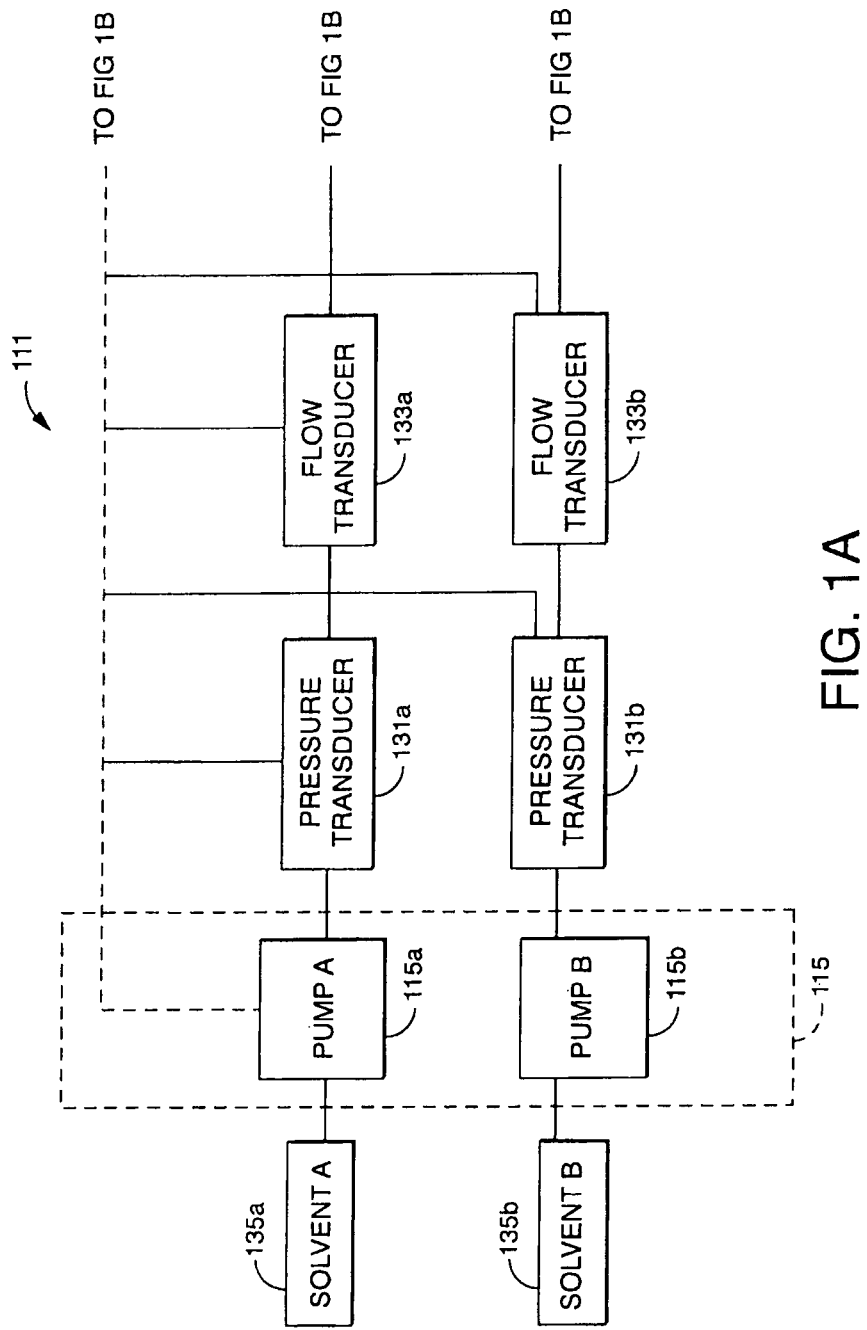
FIGS. 1A and 1B are a somewhat schematic block diagram illustrating a HPLC instrument using a solvent delivery subsystem that utilizes feed-forward principles in accordance with the subject technology, wherein matching instructions are present to illustrate how to properly connect FIGS. 1A and 1B.
Figure 1B:
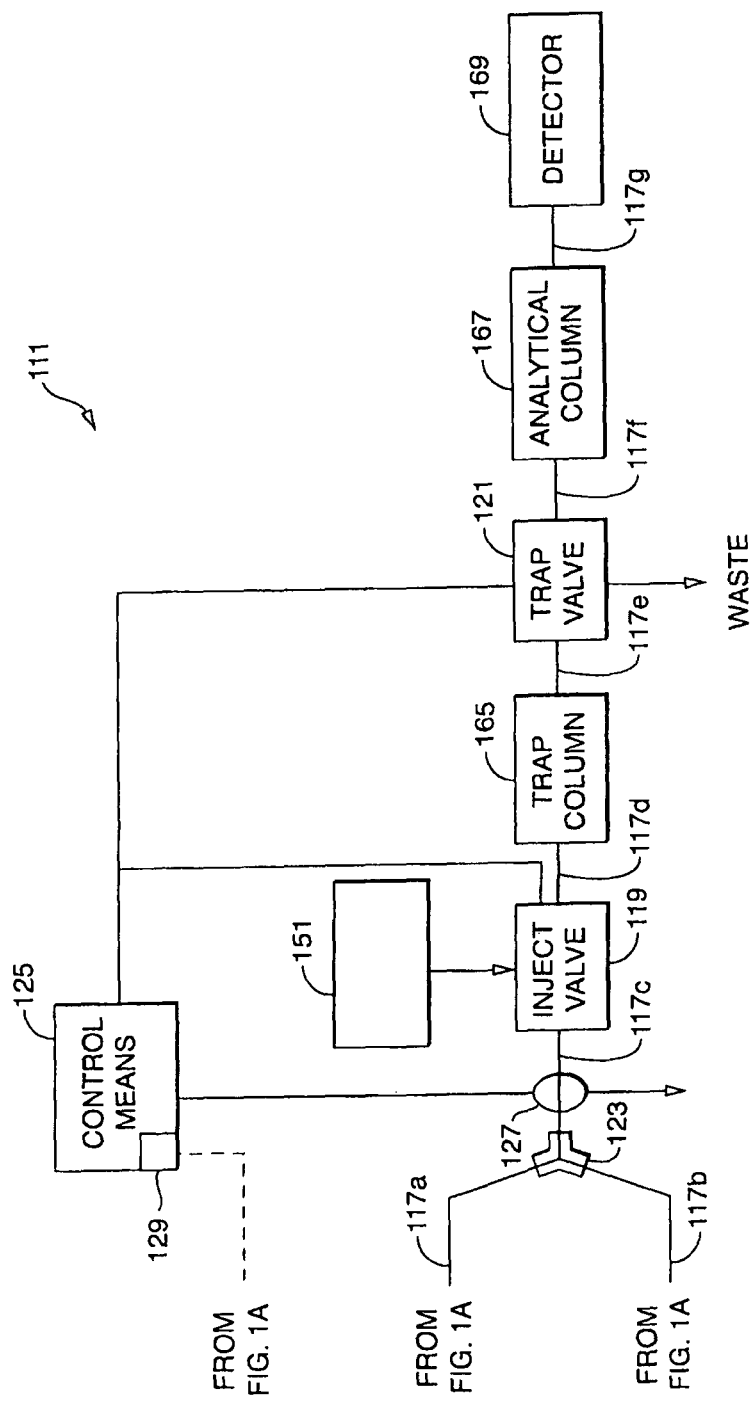

Referring to FIGS. 1A and 1B, the instrument 111 has pumps 115a, 115 b (collectively a binary pump 115) for moving respective solvents A, B contained in respective reservoirs 135a, 135b through conduits. The pumps 115a, 1115b may comprise serial and parallel pumps, turbine pumps, syringe pumps, peristaltic pumps, electrokinetic pumps, pneumatic amplifiers and fluids propelled through compressed storage devices. Typical pumps used in chromatographic applications are serial pumps powered by stepper motors. These pumps 115a, 115b are available from several venders. Waters Corporation of Milford, Mass. sells suitable pumps under the trademarks ALLIANCE®, ACQUITY®, and 600™ model pumps.

The conduits interconnect the pumps 115a, 115b with the reservoirs 135a, 135b as well as the other components of the HPLC instrument 111. These solvents may comprise any solvents use in chromatographic separations. Typical solvents may comprise a aqueous solution as one solvent (e.g., water) and an organic solvent (e.g., methanol, acetonitrile and the like). The conduits include structures like tubes, pipes, capillaries and microfluidic structures for conveying a fluid stream under a wide range of pressures. Low pressure may be atmospheric pressure but may also be a value several hundred or more above atmospheric pressure. For simplicity, the conduits are typically unlabeled and represented as lines interconnecting the components in the Figures.

Typically, the conduits are stainless steel or silica, however, other materials can be readily substituted. These materials include by way of example, without limitation, brass, aluminum, copper, titanium, ceramics, and plastics. The conduits may comprise any size; however, embodiments of the present invention have particular utility where the conduits are of a small internal diameter. For example, without limitation, the conduits or portions thereof are stainless steel tubing of 0.005 to 0.010 inch diameter. Other portions of the conduits are silica capillary of approximately 25 micrometer. In one embodiment, the conduits convey flow rates in an approximate range of 50 nanoliters per minute to 5 microliters per minute when performing analytical processes and 4 microliters per minute to 20 microliters per minute when isolating a material from a sample.

As illustrated, the pressure and flow of fluid from the pumps 115a, 115b can be monitored by pressure sensors and flow sensors, such as pressure transducer 131a and flow transducer 133a for pump 115a, and pressure transducer 131b and flow transducer 133b for pump 115b. The pumps 115a, 115b and transducers 131a, 131b, 133a, 133b are in signal communication with control means 125. Signal communication is indicated by dotted lines. For piston type pumps, the control means 125 commands the pumps 115a, 115b to move the pistons forward or backward through signals. As a result, the pumps 115a, 115b use closed-loop feedback to accurately control pressure and/or flow.

The control means 125 refers to computers, computing processing units, micro-controllers, digital signal processors, servers, analog devices programmed with suitable firmware and the like. Computers used in analytical instruments are well known to and are available from several common vendors. The control means 125 is in signal communication with pressure sensors or transducers 131a and 131b and flow sensors or transducers 133a and 133b to monitor and control the pressure and flow in accordance with FIG. 3. Commands are programmed into the firmware of control means 125 or into operating software through toolkits provided by software manufacturers. Programming of this nature is routine by individuals skilled in such art. Instrument control software is available from several vendors such as Waters Corporation of Milford Massachusetts under the trademarks EMPOWER™ or MILLINNIUM®.

Still referring to FIGS. 1A and 1B, the outputs of the pumps 115a, 115b flow into a tee fitting 123 via conduit means 117a-117g. In effect, solvent A and solvent B come together at the tee fitting 123 to form a mixture. The mixture then enters a linear valve 127, which acts as ramp means. The term "ramp means" refers to means for reducing or increasing the selected parameter gradually over time. A ramp period is the period in which these changes are effected. A ramp period is typically at least five seconds but may be much smaller or much larger depending upon the particular application. The ideal ramp period is based on the size of the fluid volumes, flow rates and pressures. Although shown as an explicit item, it is envisioned that the instrument 111 could be configured and operated to include ramp means without having the discrete linear valve 127.

The linear valve 127 can selectively convey the mixture to waste or a sample injector valve 119 for use in a trap column 165 and trap valve 121. The linear valve 127 has a range of openings and is capable of decreasing and increasing the pressure in the conduits by shunting the flow to waste or recycle. The linear valve 127 is in signal communication with control means 125 and receives commands to open or close thereby. Linear valves 127 are known in the art and are available from several vendors such as Valco of Cincinnati, Ohio.

Linear valves 127 are characterized in that the flow can be controlled in a gradual manner. Thus, the pressure and flow of the device 111 can be controlled in the manner illustrated in FIG. 3. Preferably, the linear valve 127 is controlled by a specific portion 129 of the control means 125. The linear valve control portion 129 can be a separate computer, computing processing unit (CPU), server or the same control means 125 controlling other functions, as illustrated.

When the linear valve 127 is set to allow flow forward in the instrument 111, the mixture is conveyed through the linear valve 127 to a sample injector valve 119 for use in a trap column 165 in combination with a trap valve 121. It is desirable to control the composition of the mixture such that the components of the sample are released in a reproducible manner. The tracking of pressure and flow maintains the integrity of the fluid in the conduits of the instrument 111.

Generally, "sample injector" refers to a form of valve and conduits used to bring a section of conduit holding a sample into fluid communication with conduits upstream of a column. The term "valve" refers to means to control, restrict or stop flow. Sample injectors normally comprise multiport valves and a loop (not shown) of conduit for holding a sample. The sample injector valve 119 is in fluid communication with a pressure source 151 which places sample injector valve 119 under pressure. This pressure can be matched by the control means 125 and linear valve 127. The pressure source 151 may comprise any pump or source of compressed fluid. Preferably, the pressure source 151 is a syringe pump (not shown) known in the art and available from several vendors. The term "pressure source" refers to any pump, syringe or compressed air or fluid tank and the like. Sample injectors 119 typically have syringes for withdrawing or aspirating samples.

The sample injector valve 119 and the trap valve 121 each have at least a first position and a second position. In the first position, the fluid flows and in the second position fluid does not flow. Sample injector valves 119 are sold by several venders as component parts or as part of an overall separation module. One sample injector valve is sold as a component of a separation module by Waters Corporation of Milford Massachusetts under the trademarks ACQUITY™ and ALLIANCE®. Trapping valves are sold several venders including Valco. The sample injection valve 119 places a sample in a loop of conduit (not shown).

The linear valve 127 controls at least one parameter selected from the group of flow and pressure, in the conduit means 117a-117g, in response to the placing or anticipated placing of the sample injector valve 119 and trapping valve 121 in the second position, while the instrument 111 is at one or more operating pressures. The trapping valve 121 can also selectively direct flow to waste or to an analytical column 2657 and a detector 169 without perturbations in the solvent solutions. Thus, compounds of interest captured on trap column 2655 can be effectively analyzed.

In one embodiment, one pump is selected from said first pump 115a and second pump 115b for control, ramped to pressure and the other is selected for control, ramped to flow. With respect to control ramped to flow, the flow of such pump is preferably controlled to match the flow of the pump ramped to pressure. Preferably, the pump ramped to pressure is for an aqueous solvent. And, the pump ramped to flow is for an organic solvent. For example, solvent A is an aqueous solvent. Pump 115a is commanded by control means 125 to follow ramp 141a in FIG. 3. Pump 115b tracks pump 115a with respect to flow on ramp 141b. The control means 125 commands pump 115b to maintains the correct mixture of solvent A and solvent B by coordinating the delivery of pump 115b to correspond to the delivery of pump 115a for the mixture composition. In addition, pump 115b pumps or withdraws or adds the compressed or uncompressed volume represented by the solvent B in the conduit means 117a-117g and the pump 115b as pump 115b volume changes.

Figure 2:
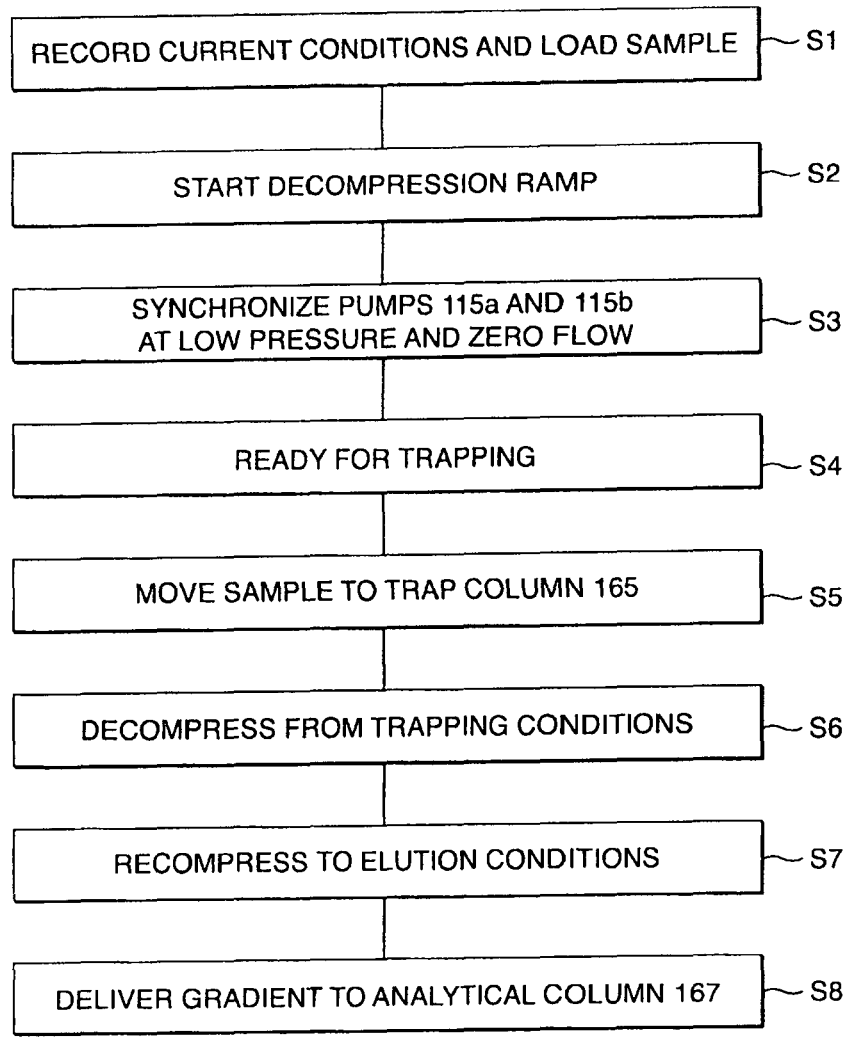
FIG. 2 is a flow diagram of a process for delivering a mixture in the instrument of FIGS. 1A and 1B in accordance with the subject technology.
Figure 3:
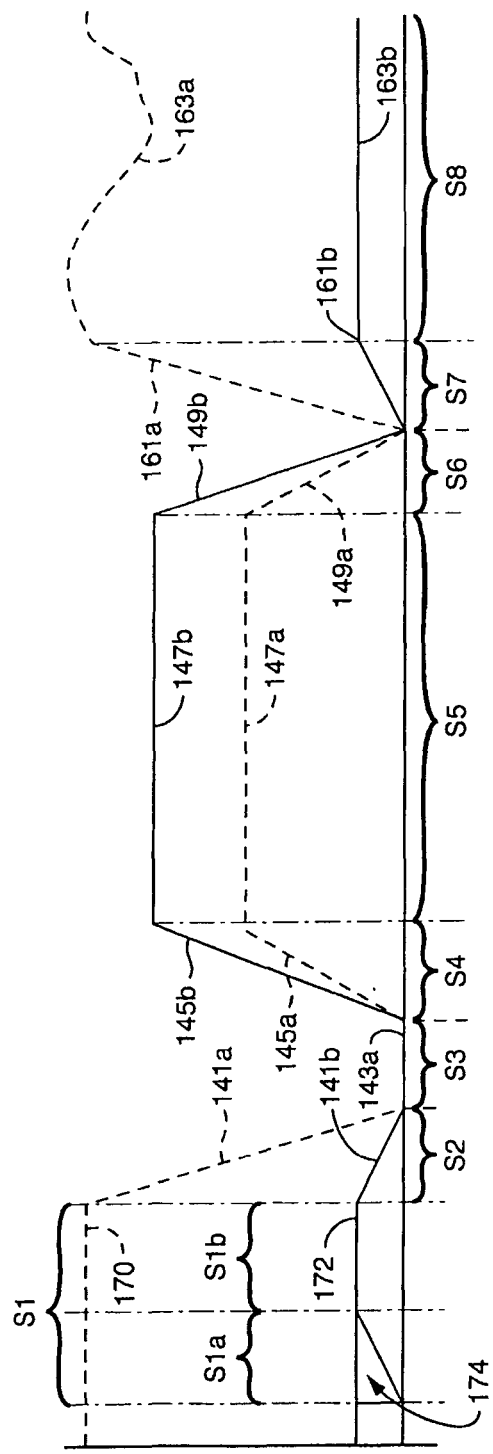
FIG. 3 is a timing diagram representing flow and pressure changes during a cycle of operation in the context of the HPLC instrument of FIGS. 1A and 1B.

Turning now to FIG. 2, a method for a cycle of operation of the instrument 111 of FIGS. 1A and 1B is shown. Most generally, the method is for use in the context of a fluid stream being conveyed in conduits under a large range of pressure and/or flow. In HPLC, the method is drawn to maintaining the integrity of a fluid despite the disparate conditions that are necessary during the different processing steps of trapping and elution. In FIG. 3, a timing diagram illustrating a pressure profile 170 and a flow profile 172 during the method of FIG. 2 is shown with the regions corresponding to the steps of FIG. 2 noted.

Referring to FIGS. 2 and 3, at step S1, the controller 125 records the current pressure and fluidic load conditions of the instrument 111. Typically, the current conditions are those desired during the previous elution run (e.g., high pressure and low flow). Thus, the trap valve 121 is set so that flow is directed to the analytical column 2657. In order to transition from elution run conditions to trapping conditions (e.g., relatively low pressure and high flow), great care must be taken to release the stored energy stored in the instrument fluid without spoiling the integrity of mixture by sloshing and backflow. Or even worse, if the backflow becomes excessive, damage to the instrument components like the column 2657 can occur.

FIG. 3 also indicates that current conditions may be those associated with instrument start up as denoted by the cross-hatched region 174. Region 174 shows that for start up conditions during an initial portion S1a of step S1, the flow is zero but is ramped up to analytical flow. In other words, the cross-hatching region 174 is an indication of the alternative lower flow profile 172 from start up conditions until the instrument 111 can ramp to initial gradient flow and composition.

Preferably during portion S1a, the instrument 111 also advantageously loads the sample into the loop of the inject valve 119. The sample is loaded by setting the inject valve 19 to load and using the pressure source 51. Further, the instrument 111 downloads the setup parameters for the next run. These setup parameters are provided to the control means 125.

During the remaining portion S1b of step S1, the analytical flow has been reached and, thus, the flow profile is consistent between the two alternative approaches. Further, the instrument 111 stores the current parameters for the next run. These current parameters of pressure and fluidic load, R, are provided to the control means 125 as described below with respect to step S7.

At step S2, the instrument 111 starts the decompression ramp to enable trapping conditions. The control means 125 commands the linear valve 127 to decrease pressure in a first ramp 41a with respect to pressure. Simultaneously, the control means 125 commands the pump 115a to zero pressure and the pump 115b to zero flow preferably with feed forward compensation (e.g., a hybrid decompression ramp 141a). The term "feed forward compensation" generally means open-loop compensation as will be described in more detail below. Preferably, step S2 lasts about 30 seconds.

At step S3, the instrument 111 is at a low pressure and flow condition 143a. Although this low pressure 143a can be atmospheric pressure, as illustrated, the low pressure 143a can also be well above atmospheric to correspond to a pressure in the sample injector valve 119. To accomplish this ramp 141a, the linear valve 127 vents to waste and the control means 125 operates both pumps 115a, 115b set to zero flow. In effect, the energy stored in the compressed fluid is released without or at least minimizing backflow and sloshing. The pumps 115a, 115b become synchronized. Preferably, step S3 lasts about 5 minutes.

At step S4, the instrument 111 readies for the trapping process by directing the trap valve 121 to the trapping position, i.e., the trap valve 121 directs flow to waste. Both pumps 115a, 115b ramp to the desired trapping conditions of relatively low pressure and high flow as illustrated by ramps 145a, 145b, respectively. To accomplish the ramps 145a, 145b, the control means 125 commands the linear valve 127 to increase pressure in the conduits up to the operating pressure 147a and flow 147b.

Depending upon the flow generated by each pump 115a, 115b, the mixture exiting the tee 123 can be controlled. The control means 125 also readies the inject valve 119 to commence injection of the sample in order to move the sample from the loop to the trap column 165. Preferably, step S4 lasts about 30 seconds.

At step S5, the instrument 111 reaches equilibrium at the trapping pressure 147a and trapping flow 147b with the desired composition of the mixture. Preferably, instrument 111 delays for about 1 minute to allow full equilibrium prior to commencing injection of the sample. Upon reaching equilibrium, the sample is moved from the loop to the trapping column 165 by setting the inject valve 119 to the injection position. Because of the relatively higher flow 147b, the time to transfer the sample can be fast, on the order of minutes. Preferably, the user selects the time period of trapping to insure that the sample is effectively moved to the trap column 165. In one embodiment, step S5 lasts about 5 minutes.

At step S6, hybrid decompression occurs after the trapping operation is complete. Although less than during an elution run, the significant energy storied in the instrument 111 needs to be efficiently and effectively dissipated without ruining the integrity of the mixture in the conduits. The hybrid decompression includes setting the pressure of pump 115a to zero while setting the flow of pump 115b to zero preferably with feed forward. As a result, the pressure declines to about atmospheric as shown by ramp 149a and the flow moves to zero as shown by ramp 149b.

Again, to achieve these ramps 149a, 149b, the control means 125 commands the linear valve 127 to gradually vent to atmosphere. The inject valve 119 is set to the load position, i.e., the loop for holding the sample is removed from the fluid path to reduce the amount of overhead that needs dissipation and subsequent recompression. The trap valve 121 closes off to waste and directs flow to the analytical column 2657. Upon reaching the minimal flow and pressure conditions at the end of step S6, the instrument 111 can adjust settings to redirect fluid flow and the like while maintaining the integrity of the fluid therein. Preferably, step S6 lasts about 30 seconds.

At step S7, the instrument 111 performs hybrid recompression to accomplish an elurtion run without incurring an undesirably long recompression time because of the relatively large volume of stored energy required to compress the fluid stream back up to the operational pressure. Prior to starting the hybrid recompression, the control means 125 acquires the pressure and fluidic load parameters stored at step S1b.

If the pressure and flow are the same as was previously used, at least initially, the instrument 111 attempts to return to the previous values. If the pressure and flow are different, the instrument 111 extrapolates new settings based upon the stored value of fluidic resistance R. For example, if the step S1b parameters were a system pressure Ps of 9,000 PSI at a set flow Qs of 0.350 microLiters per minute, then the fluidic resistance, Rs=Ps/Qs, of about 25,700 psi/μL/min would be calculated and stored in memory. The instrument 11 would use the following formula to determine the new settings:

$$P\text{new} = Q\text{new} * Rs$$

In order to achieve the new settings, the control means 125 commands the linear valve 127 to increase pressure in the conduits to the operating pressure as shown in ramp 161a and to the operating flow as shown in ramp 161b. At the same time, the control means 125 runs the pumps 115a, 115b under closed loop feedback control. By setting the pumps 115a, 115b to a high pressure and allowing the flow to increase to meet the pressure for a brief interval, the set flow and pressure parameters are achieved very quickly without ruining the integrity of the mixture. In one embodiment, step S7 lasts about 30 seconds or preferably less.

The ramps 141a, 141b, 145a, 145b, 149a, 149b, 161a and 161b are depicted as being linear; however, such ramps may be non-linear as long as the slope, indicative of the change in pressure over time is managed. A preferred slope is not greater than approximately 10,000 pounds per square inch (psi) per second. More preferably, the slope is in the range of 10 to 1,000 psi per second, and, more preferably, 100 to 500 psi per second.

At step S8, once the instrument 111 reaches the desired setting for flow and pressure, the flow enters a steady state condition during the elution run as shown by flat area 163b. In contrast, the pressure may fluctuate as shown by varying region 163a. During step S8, the sample is delivered to the analytical column 167 for analysis.

Feed Forward Embodiments

Referring now to FIGS. 4A-10, another HPLC instrument 211 using feed forward is referred to and shown in various views. As will be appreciated by those of ordinary skill in the pertinent art, the instrument 211 utilizes similar principles to the instrument 111 described above. Accordingly, like reference numerals preceded by the numeral "2" instead of the numeral "1", are used to indicate like elements whenever possible. A primary difference of the instrument 211 in comparison to the instrument 111 is the lack of a linear valve 127.

Referring to FIGS. 4A and 4B, another direct-flow nanoscale HPLC instrument 211 that uses open-loop feed forward compensation in accordance with the subject technology is shown. The instrument 211 is shown in somewhat schematic form with a plurality of parts grouped and collectively referred to as a binary gradient pump 220. The binary gradient pump 220 is designed for use in analytical-scale chromatography and modified to deliver precise gradients for nano-flow LC applications by incorporating in-line flow transducers 233A, 233B, used in conjunction with closed-loop feed back control provided by the control means 225. In one embodiment, the flow transducers 233A, 233B are anemometer type flow transducers.

Pump 215A represents an independent high-pressure pump that sources one of two mobile-phase solvents (e.g., aqueous) from a reservoir supply 235A to the mixing tee 223. Pump 235A may be comprised of two reciprocating pumps for smooth flow delivery. The solvent flow at the outlet of pump 235A is directed through an inline pressure transducer 231A and an inline nano-flow transducer 233A. The pressure transducer 231A provides a measurement of the instrument operating pressure and the flow transducer 233A provides direct nano-flow measurement of the solvent A fluid stream into the mixing tee 223. Through closed-loop control, the control means 225 is able to maintain accurate flow delivery in the presence of large parasitic flow leakages upstream from the flow transducer 233A, due to high-pressure seals and check valves of pump 215A. Likewise, pump 215B represents a similar independent high-pressure pump having a corresponding pressure transducer 231B and flow transducer 233B that sources the complementary mobile-phase solvent (e.g., organic) from a reservoir supply 235B to the mixing tee 223.

The control means 225 establishes the desired user-set bulk flow to the instrument 211 and compositional mix ratio of the two solvents by regulating the delivery flow of each pump 215A, 215B into the mixing tee 223. By having both pressure and flow transducers 231A, 231B, 233A, 233B in each pump's solvent stream, the instrument 211 provides great flexibility with two fundamental control modes of operation.

Conduits 240A, 240B are series restrictors such as, for example, short lengths of capillary tubing, to provide passive fluidic decoupling between the two pumps 215A, 215B to stabilize the inherent interactions of the two flow control loops across the mixing tee 223. The restrictors or conduits 240A, 240B are intentionally located downstream of the flow transducers 233A, 233B to minimize volume between the transducers 233A, 233B and the tee 223.

The solvent stream from the binary gradient pump 220 is conveyed via a conduit (e.g., a short capillary tube) to a sample injector valve 219 that introduces one or more sample analytes from a sample reservoir into the fluid stream, which is directed to one or more separation columns 265, 267, depending on the configuration. The separated analytes from the analytical column 267 are directed to a detector 269 such as a mass spectrometer, UV detector and/or the like.

As shown in FIG. 4B, the instrument 211 features a simplified trapping scheme, operating in a forward flush mode, comprising a trapping column 265, a trapping valve 221, and an analytical column 267. The binary gradient pump 220 performs both operations of sample loading/trapping and gradient delivery as described below. While FIG. 4B indicates a "forward flush" scheme, the subject technology is applicable to other trapping approaches such as "reverse flush" as is known to those familiar with the art of trapping schemes. During trapping operation as shown, the binary gradient pump 220 provides a fixed solvent composition (e.g., very high %A (aqueous) very low %B organic) at a relatively high flow rate (e.g., 5 to 15 uL/min) with the trapping valve 221 opened to waste. As a result of the very high fluidic restriction of the analytical column 267, the solvent stream is directed to waste. The sample analytes are loaded onto the trapping column 265 while the eluent components that are undesirable or harmful to the analytical column 267 (e.g., buffers, salts, and the like) are flushed away to waste. When trapping completes, the binary gradient pump 220 stops the trapping flow and reconfigures the instrument 211 for the analytical separation. The trapping valve 221 closes, thus directing the fluid stream to the analytical column 267. The binary gradient pump 220 then commences with the gradient run at the preprogrammed nano-flow rate and time-programmed solvent composition profile. As noted in FIG. 4A, the "Set Flow", percentage of solvent A and percentage of solvent B are entered by a user into the control means 225.

In another embodiment, the instrument 211 operates in direct injection mode without the trapping column 265. In that mode, a short capillary tube (not shown) replaces the trapping column 265, and the trapping valve 221 is kept closed, directing the fluid stream to the analytical column 267. The injection of the sample analytes takes place during the start of the gradient run.

Figure 5:
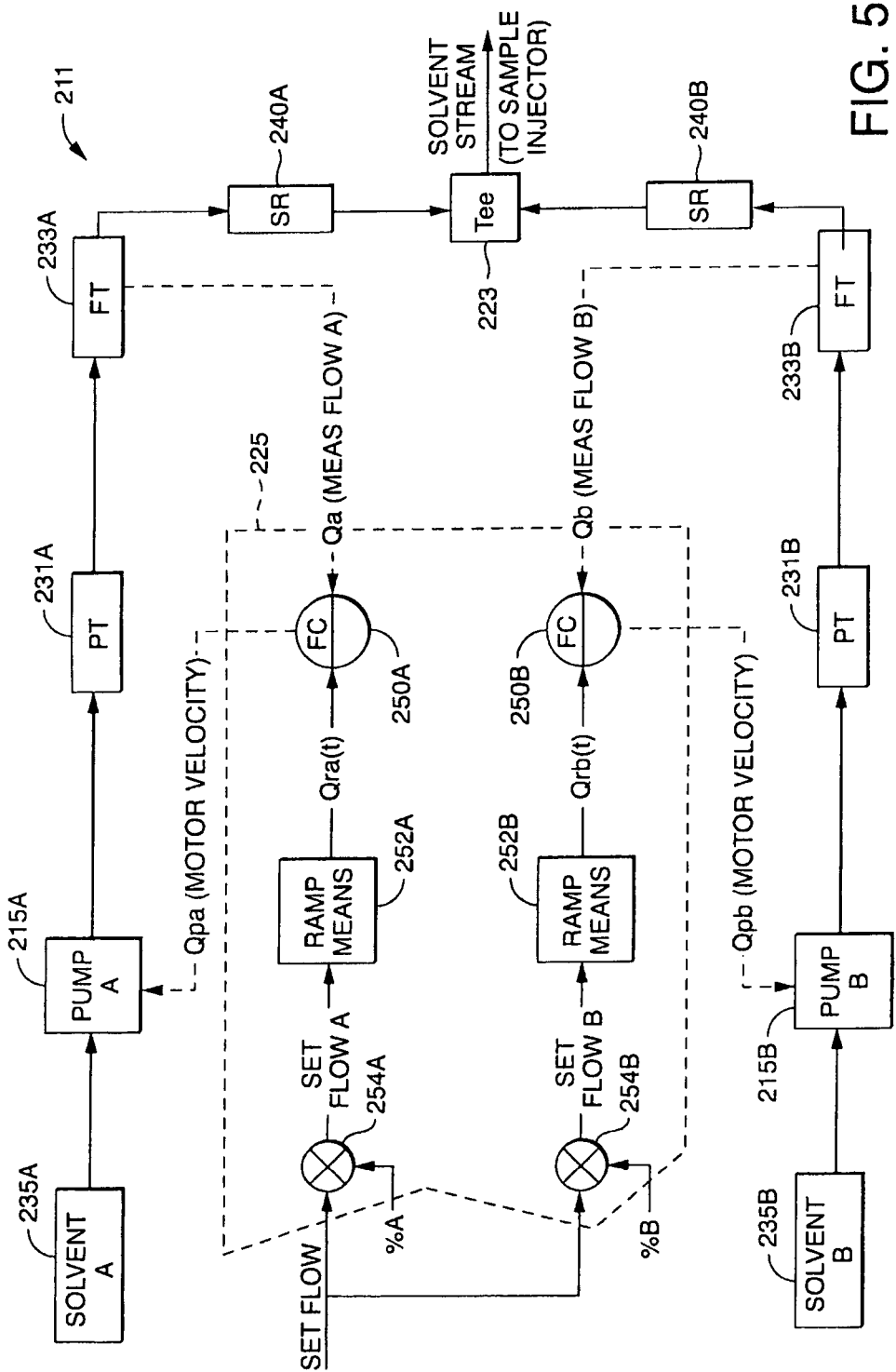
FIG. 5 is a somewhat schematic representation of the control means of FIGS. 4A and 4B in greater detail to illustrate a flow control strategy in accordance with the subject technology.

Referring now to FIG. 5, a somewhat schematic representation of the control means 225 in greater detail is shown to illustrate a flow control strategy. As noted above, prior art systems suffered from the loss of solvent compositional control during operation at very high system pressures, such as greater than 5,000 psi, and between the operations of trapping or direct injection runs whenever the flow to the system started or stopped. The control means 225 establishes the user-set bulk flow to the instrument 211 (Set Flow) and the user-set compositional solvent ratios (% A and % B) through two flow controllers 250A, 250B for each solvent pump 235A, 235B, respectively. The set flow, percentage of solvent A and percentage of solvent B are input to each path, respectively, along summing junctions 254A, 254B.

Each flow controller 250A, 250B is implemented as a PID feed back controller and behaves essentially as a servo loop, responding to either an instrument flow change or a solvent composition change, either of which is conveyed as a new flow set point. The flow controllers 250A, 250B compare the current flow set point or reference input (Qra, Qrb) to the measured flow (Qa, Qb) entering the tee 223 and, in the case of stepper motor controlled piston pumps, produce the appropriate motor velocity signal, which drives the necessary pump volumetric flow rate (Qpa, Qpb) into the instrument 211 so that the reference flow (Qr) is satisfied. Similarly, for other pumping strategies, appropriate signals Qpa, Qpb would be generated to satisfy Qr.

Set-flow changes are conveyed to the flow controllers 250A, 250B through a linear ramping function, represented by the ramp means 252A, 252B. For each pump 215A, 215B, the ramp means 252A, 252B passes the new flow set point to the reference set point (Qr) of the respective flow controller 250A, 250B incrementally as a linear function with respect to time over a ram ping interval Tr that assures good servo tracking between the two flow controllers 250A, 250B. Generally, a reasonable value for Tr is about five times the time constants of the flow transducers 233A, 233B. In a preferred instrument 211, the time constant of the flow transducers 233A, 233B is about 5 seconds, so a ramping time interval Tr of 30 seconds is preferred. The ramp means 252A, 252B maintains the prior history of the respective flow controller's set point and for each new user-set value, the control means 225 calculates the following: the direction; the total change value delta Flow (equal to newSetFlow−presentSetFlow); and the ramp rate Rp (equal to delta Flow/Tr), which governs the incremental updates to the reference input (Qr) of the flow controller 250A, 250B.

As can be seen from FIG. 5, each ramp means 252, flow controller 250, transducer 231, 233 and pump 215 form a flow control servo loop. For relatively small changes in composition (i.e., complementary flow changes between the two flow control servo loops) or bulk flow changes to the instrument 211 (i.e., changes within the band width of the flow transducers), the two flow control servo loops are able to maintain good composition control, hence flow tracking, sufficient to do HPLC chromatography. Such is the case during the programmed gradient run.

However, when making very large flow changes, accompanied with large back pressure changes, the tracking ability of the two flow controller servo loops breaks down, and composition control is lost, resulting in composition error in the fluid stream of the instrument 211 and a loss of chromatography. For example, when the flow in the instrument 211 is stopped or started with very restrictive capillary columns, composition error can occur. This problem is particularly problematic during trapping when transitioning the bulk flow of the instrument 211 from the end of the trapping phase (e.g., high-flow and moderate pressure) to the starting analytical flow conditions (e.g., nano flow and very high pressure) at which gradient delivery begins.

The ramp means 252A, 252B alone can limit large set point changes to the flow controllers reasonably effectively with lower operating pressures, such as an operating pressure of 5,000 psi. However, if not properly compensated for, a higher operating pressure, such as 10,000 psi, to enable operating with much longer capillary columns, yields at least a partial loss of composition control, due to severe mistracking of the flow controllers.

The cause of the mistracking is due to the very large cylinder volumes of the pumps 215A, 215B relative to the nanoscale of flow delivery to the instrument columns 265, 267. Since the mobile phase solvents used in these LC applications are relatively compressible at the aforementioned operating pressures, the captive volume of these fluids requires considerable energy storage before steady-state flow can be achieved into the mixing tee 223. This energy storage manifests itself as a compressible volume change of the instrument fluid and is directly proportional to the solvent compressibility and captive volume, and proportional to the square of the operating pressure. The stored energy is supplied by each pump 215 as an additional 'charging' flow while the pressure is changing and is much greater than the flow being controlled into the mixing tee 223. Because the solvents A, B typically have much different fluid compressibility, the effective charging flows between the two respective pumps 215A, 215B differ by the ratio of their compressibility as does the volume changes across the mixing tee 223. Thus, the inability of the flow controllers 250A, 250B to manage the considerable imbalance of charging flows and volumes at the mixing tee 223 creates a loss of composition control.

Fluidics Model

To illustrate the dynamics of the loss of composition control and how the instrument compensates for the limitations of the flow controllers 250A, 250B, a simplified analytical model of the fluidics is now presented. The compressibility of a fluid is defined as the relative volume change of a fluid as a response to a pressure change and is expressed mathematically as:

$$\beta = -\frac{1}{V} \cdot \frac{\partial V}{\partial P}$$

where V is the volume of the system, and the partial derivative expresses the change in volume to the change in pressure. In thermodynamic terms, the compressibility is defined by the conditions or process by which the partial differential is taken (e.g., adiabatic/constant entropy or isothermal/constant temperature).

The differential change in volume relative to the change in pressure is also expressed as fluid capacitance, which is the capacity of a fluid to store energy. Thus, the fluidic capacitance becomes:

$$C = \beta \cdot V_o$$

where $\beta$ is the fluidic compressibility and $V_o$ is the captive volume of the system. Using the simple Ohmic relation from electrical circuits, the fluidic resistance is represented as:

$$R = \Delta P/Q$$

where $\Delta P$ is the pressure drop across a restrictive element, and Q is the flow rate through the element. Resistance R is basically proportional to the length of a fluidic element and the viscosity of the fluid flowing therethrough.

Figure 6:
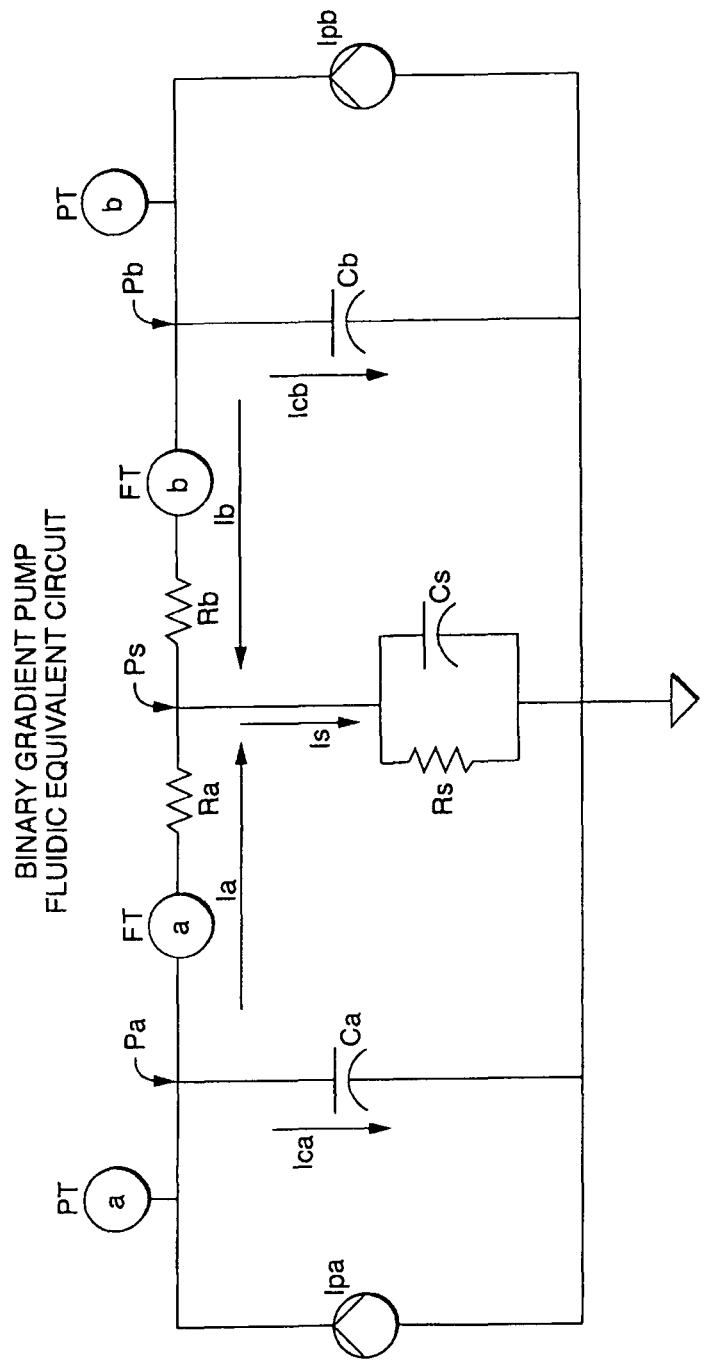
FIG. 6 is an electrical circuit analog to the instrument of FIGS. 4A, 4B and 5 in accordance with the subject technology.

Using the basic lumped-parameter elements of capacitance and resistance analogous to electrical circuits, an equivalent fluidic circuit of the instrument 211 is presented in FIG. 6. In the analogy, currents "I" represent volumetric flow "Q" in units of µL/min. Voltages represent pressures in psi and capacitance "C" represents the fluidic energy storage of the fluids and is expressed in units of µL/psi. Resistance "R" represents fluidic restriction to flow in units of psi/µL/min.

Relating the fluidic model in FIG. 6 to the flow control servo loops in is FIG. 5, Ipa and Ipb are two dependent current or flow sources that represent the volumetric flow delivered by both pumps A and B into the instrument 211, respectively. The flows Ipa, Ipb are directly proportional to the commanded velocity of the pump motor actuators. PTa and PTb represent the two in-line pressure transducers 231A, 231B, respectively. The pressure transducers 231A, 231B measure the node pressures Pa and Pb, respectively, at the pumps 215A, 215B. Likewise, FTa and FTb represent the two in-line flow transducers 233A, 233B, respectively. The flow transducers 233A, 233B measure the two controlled flows Ia and Ib, respectively, into the mixing tee 223.

The sum of the two flows Ia and Ib at the mixing tee 223 results in the flow Is out of the mixing tee 223. The effective load of the instrument 211 is represented by resistance Rs, which is primarily the fluidic resistance of the columns 265, 267 at the end of the fluidic circuit, where Cs represents a lumped fluidic capacitance of the instrument downstream of the mixing tee 223. The capacitance Cs is primarily comprised of the volume of the sample loop of the injector valve 219 and the volume of the trapping column 265. The capacitance Cs is much smaller than the pump capacitances Ca, Cb.

Ra and Rb represent the fluidic resistance of the two capillary restrictors 240A, 240B, respectively. While not necessary, the resistances Ra, Rb are made roughly equal by making the respective lengths in proportion to the viscosities of solvents A, B. The resistances Ra, Rb are very small relative to the combined resistance Rs of the capillary columns 265, 267. For example, the resistances Ra, Rb are about 40 psi/µL/min, whereas the resistance Rs of a 75 µm ID×150 mm×1.7 µm particle capillary column is approximately 25,000 psi/µL/min for water.

Ps is the system back pressure resulting from the system flow Is into the columns 265, 267 or instrument resistance Rs. Since the capillary restrictors are so much smaller than Rs, each of the measured pump pressures Pa, Pb are a reasonable measure of the instrument back pressure Ps. Ca and Cb represent the lumped fluidic capacitance of each pump 215A, 215B, respectively, and comprises the captive volume of: the final delivering pump cylinder, including its displacement stroke volume and internal dead volume between its inlet valve (or check valve, which is not shown) and outlet port, the pressure transducer, and all the connecting conduits up to but not inclusive of the flow transducers 231, 233, respectively. In one embodiment, the captive volume of the delivering pump cylinder and interconnecting conduits up to the flow transducers is about 160 uL. For the aqueous pump 215A, the fluid compressibility constant β for water is 3.12e−6/psi. Thus the fluid capacitance of the A pump is about:

$$Ca = 3.12e-6/\text{psi} * 160 \, \mu L = 0.0005 \, \mu L/\text{psi}$$

For the organic pump 215B, the fluid compressibility constant β for acetonitrile (ACN) is 7.34e−6/psi, which is 2.35 times as compressible as water. Thus, the fluid capacitance of the B pump is about:

$$Cb = 7.34e-6/\text{psi} * 160 \, \mu L = 0.00118 \, \mu L/\text{psi}$$

Ica and Icb represent the compressibility 'charging' or 'discharging' flows into or out of the respective pump fluidic capacitances Ca, Cb whenever the node pressures Pa, Pb change. Using the electrical equivalency, the compressibility flows are expressed as follows:

$$I_{ca} = C_a \frac{dP_a}{dt} \quad I_{cb} = C_b \frac{dP_b}{dt}$$

To put the limitations of the feedback control strategy in perspective, consider the following scenario in which the flow ramps from zero to the initial conditions of the gradient over the ramping interval Tr of 30 seconds. Such is the case either following trapping or with direct injection. During the ramping interval, the composition is held constant with a very high aqueous to organic mix ratio (e.g., 97% A, 3% B). For a target flow rate Is of 350 nL/min with the aforementioned column, a steady-state system pressure Ps of about 9,000 psi is to be achieved. With the ramping scheme, the instrument pressure Ps should also ramp linearly from zero to 9,000 psi. The change in fluid volume for the A pump needed to compress the system to 9,000 psi is:

$$\Delta V_a = C_a * \Delta P = 0.0005 \, \mu L/\text{psi} * 9{,}000 \, \text{psi} = 4.5 \, \mu L$$

Since the compressibility of the B solvent is 2.35 times that of the A solvent, the corresponding volume change of the B pump is about 10.6 µL.

For example, iln order to ramp the system pressure to 9,000 psi over the second ramp interval, the pump 215A must supply a sustained average 'charging' flow Ica of:

$$I_{ca} = C_a \frac{\Delta P_a}{\Delta T} = 0.0005 \, \mu L/\text{psi} * 9{,}000 \, \text{psi}/30 \, \text{sec} = 9.0 \, \mu L/\text{min}$$

while ramping an associated controlled flow Ia from zero to a target value of 0.97*350 nL/min or about 340 nL/min. Likewise, the pump 215B must supply a sustained average 'charging' flow Icb of:

$$I_{cb} = C_b \frac{\Delta P_b}{\Delta T} = 0.00118 \, \mu L/\text{psi} * 9{,}000 \, \text{psi}/30 \, \text{sec} = 21.2 \, \mu L/\text{min}$$

while ramping an associated controlled flow Ib from zero to a target value of 0.03*350 nL/min=11 nL/min.

If composition control at the outlet of the tee is to be maintained, then the compression or charging flows at the pump heads must be maintained at the correct ratio of the two solvent compressibility factors, independent of the composition ratios. If this requirement is not met, then the delicate differential tracking of the node pressures Pa, Pb across the inlet ports (not shown) of the mixing tee 223 necessary to maintain the proper mix ratio of the controlled inlet flows Ia, Ib will no longer be maintained by the flow controllers 250A, 250B. If the differential pressure upset is severe enough, then one of the node pressures Pa, Pb will drop below the instrument pressure Ps causing a flow reversal for that leg or side of the mixing tee 223. In this situation, the dominating pump with the higher node pressure, Pa or Pb, saturates the solvent mixture at the outlet (not shown) of the mixing tee 223 and contaminates the other pump's flow transducer, 233A or 233B as the case may be. Thus, due to the structure and volume scale of the fluidic circuit, the pressure differential across the mixing tee is much more strongly dependent on the charging flows as compared with the two controlled flows into the tee. This poses a very ill-conditioned problem for the feed back controllers, which can only react to errors in the rather small inlet flows into the mixing tee compared with the much larger uncontrolled charging flows, which are in the order of almost 2,000 to 1 for the organic pump.

For example, at the onset of the ramping operation, there will be virtually no measurable flows into the mixing tee 223 until the capacitance of each pump head begins to charge. The flow controller's proportional action would rail the command signal velocity of each pump motor (not shown) to the high limit of 100 uL/min, which is about 10 times the average charging flow of the aqueous pump 215A, but barely 5 times the average charging flow of the organic pump 215B. Thus, the time duration in which both pumps 215A, 215B remain open loop is different, being about 2.7 seconds for the aqueous pump 215A, and about 6.3 seconds for the organic pump 215B. Clearly, there is an overlapping interval of at least 3 seconds in which both pumps 215A, 215B are open loop but flowing at the same flow rate! Thus, the feed back controllers have no knowledge or direct measurements of the very high charging flows caused by the discharged state of both pump heads and are unable to maintain composition control. This problem has a complimentary behavior when the system flow is ramped to zero from the typical ending gradient conditions. In this case, the stored energy of each pump 215A, 215B is released back into the system 211 when the compressed volumes expand. Since the organic pump 215B has more capacitance or energy storage, the fluid of the aqueous pump 215B expands more than the fluid of the organic pump 215A, causing the organic pump 215B to undesirably 'burp' out into the outlet stream and back flow into the other transducer 233A. Such is the case when the system 211 transitions from the previous run to begin either a direct injection or a trapping operation for the next run.

Figure 7:
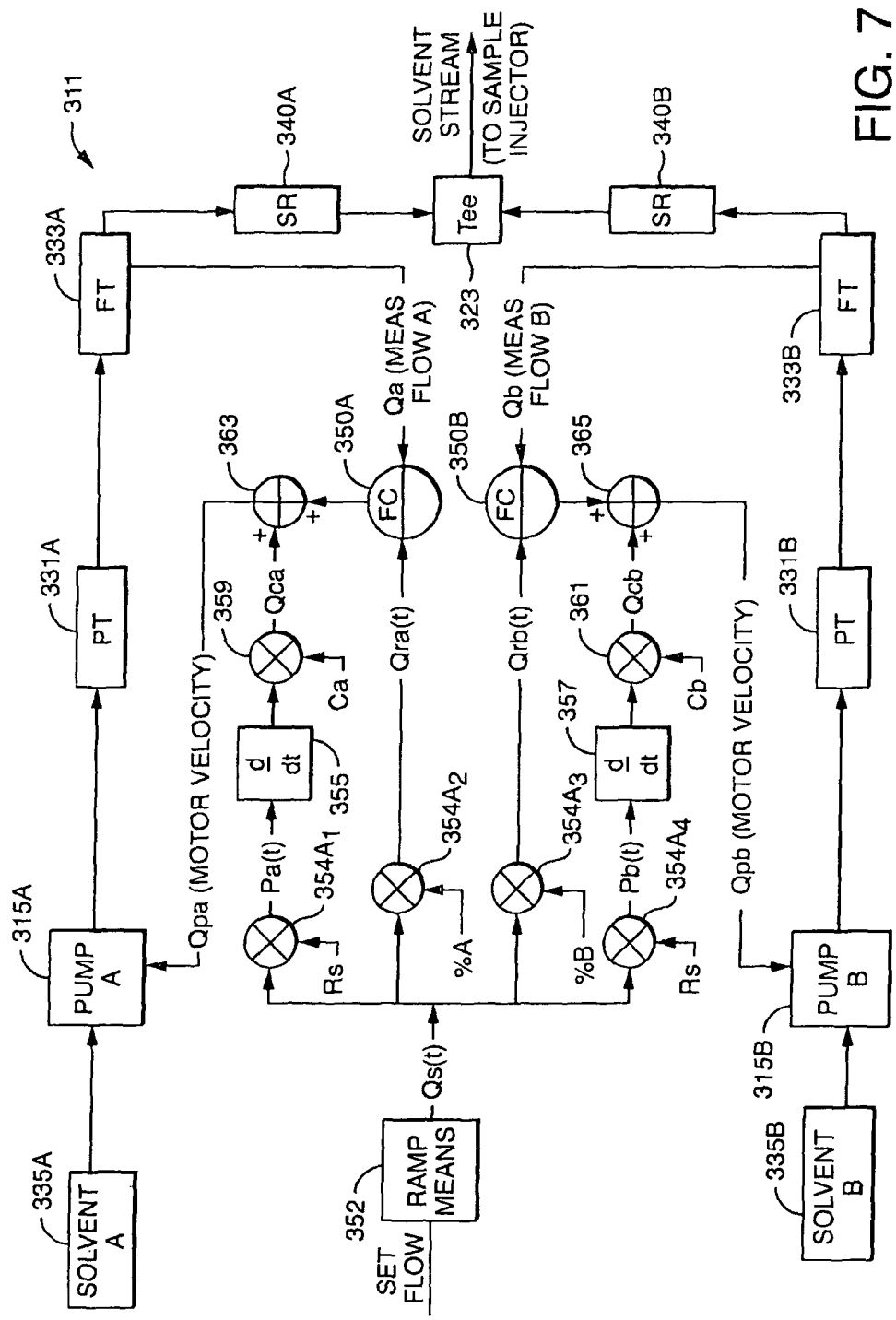
FIG. 7 is a somewhat more detailed version of the instrument of FIGS. 4A and 4B is shown to more particularly illustrate the usage of feed forward compensation in accordance with the subject technology.

Referring to FIG. 7, a somewhat more detailed version of the instrument 311 of FIGS. 4A and 4B is shown to more particularly illustrate the usage of feed forward compensation in accordance with the subject technology. As will be appreciated by those of ordinary skill in the pertinent art, the instrument 311 utilizes similar principles to the instruments described above. Accordingly, like reference numerals preceded by the numeral "3" are used to indicate like elements whenever possible. A primary addition of the instrument 311 in comparison to the instruments 111, 211 is the inclusion of signal summing and multiplying junctions and analogous current references as depicted in the fluidics model of FIG. 6.

In overview, the corrective feed forward control scheme is based on separation of the bulk energy storage, i.e., the bulk fluid compressibility of the pump heads from the feed back control of flow (and composition) during the flow ramping operation. The feed-forward scheme manages the large back pressure changes required to compress and decompress the bulk captive head volumes independently from the closed-loop flow controllers 250A, 250B. The feed forward scheme applies a control law to the tandem movement of the pump plungers (not shown) such that the storage or release of compression energy of the pump heads (not shown) are controlled in such a manner to preserve the proper compositional flows, Qa and Qb, at the input ports to the mixing tee 23. The feed forward control action effectively balances the two node pressures, Pa and Pb, so that the sloshing of liquid across the mixing tee 323 is within acceptable error tolerance of composition.

From the perspective of the feed back controllers, the feed forward scheme off loads the bulk capacitive load or disturbance to the flow controllers during the flow ramps, effectively making the captive volume of the pump heads virtually disappear. A primary load disturbance to the controlled flows is delta P, or change in node pressure from the driving pump head. Thus, the disturbance flow Qdist presented to each flow controller is proportional to delta P. This delta P gives rise or fall to the very large compression or decompression flow Ic that flows into and out of the captive head volume whenever large pressure changes occur due to the large bulk flow changes. The feed forward loop effectively estimates the necessary charge or discharge flow Ic that must be supplied or absorbed by each pump 315A, 315B, independently from the controlled flows into the mixing tee 323, so that the feedback controllers can maintain the correct compositional mix ratio while the system pressure ramps in response to only the change in bulk flow to the system 311. Referring back to FIG. 6, generally, feed forward control law is simply the charging or discharging flow of the head volume capacitance in response to a change in pressure:

$$Q\text{feedforward} = Ic = C\, dp/dt$$

and the pressure change is the estimated or measured disturbance function. Referring now to FIG. 7, the ramp means 352 provides the desired bulk flow ramping function to the control strategy. For the A pump 315A, using a measure of the system resistance Rs stored from a previous run by the control means, an estimate of the anticipated system pressure ramp Pa is derived at multiplier 254A 1. The feed forward scheme computes the pressure disturbance signal by taking the derivative operation 255 of Pa. The feed forward control law Qca is calculated by multiplying the derivative of Pa by the measured capacitance Ca of pump A at 259. The feed forward correction is summed into the command signal from the flow feed back controller 350A at summing junction 263. Likewise, the B pump 315B derives its feed forward correction signal via operations, 254A4, 257, 261, and 265. In practical applications, the feed forward calculation need not take the actual derivative of the pressure signal, with the control scheme presented in FIG. 7. Instead, the ramp rate Rp, computed by the ramp means 352 (cite paragraph 0123), is the derivative of the pressure ramp signal and is simply multiplied by the capacitance Ca to produce the feed forward signal Qca.

In another embodiment, the feed forward estimate of the disturbance signal Pa could replaced by an actual measurement provided by pressure transducer 331A. However, noise is always present with the signal and adequate means of filtering must be provided appropriate to taking the derivative of a signal.

Referring now back to FIG. 7, a somewhat more detailed version of the instrument of FIGS. 4A and 4B is shown to more particularly illustrate the application of feed forward compensation in accordance with the subject technology.

Further Refinements of Feed Forward

Figure 8:
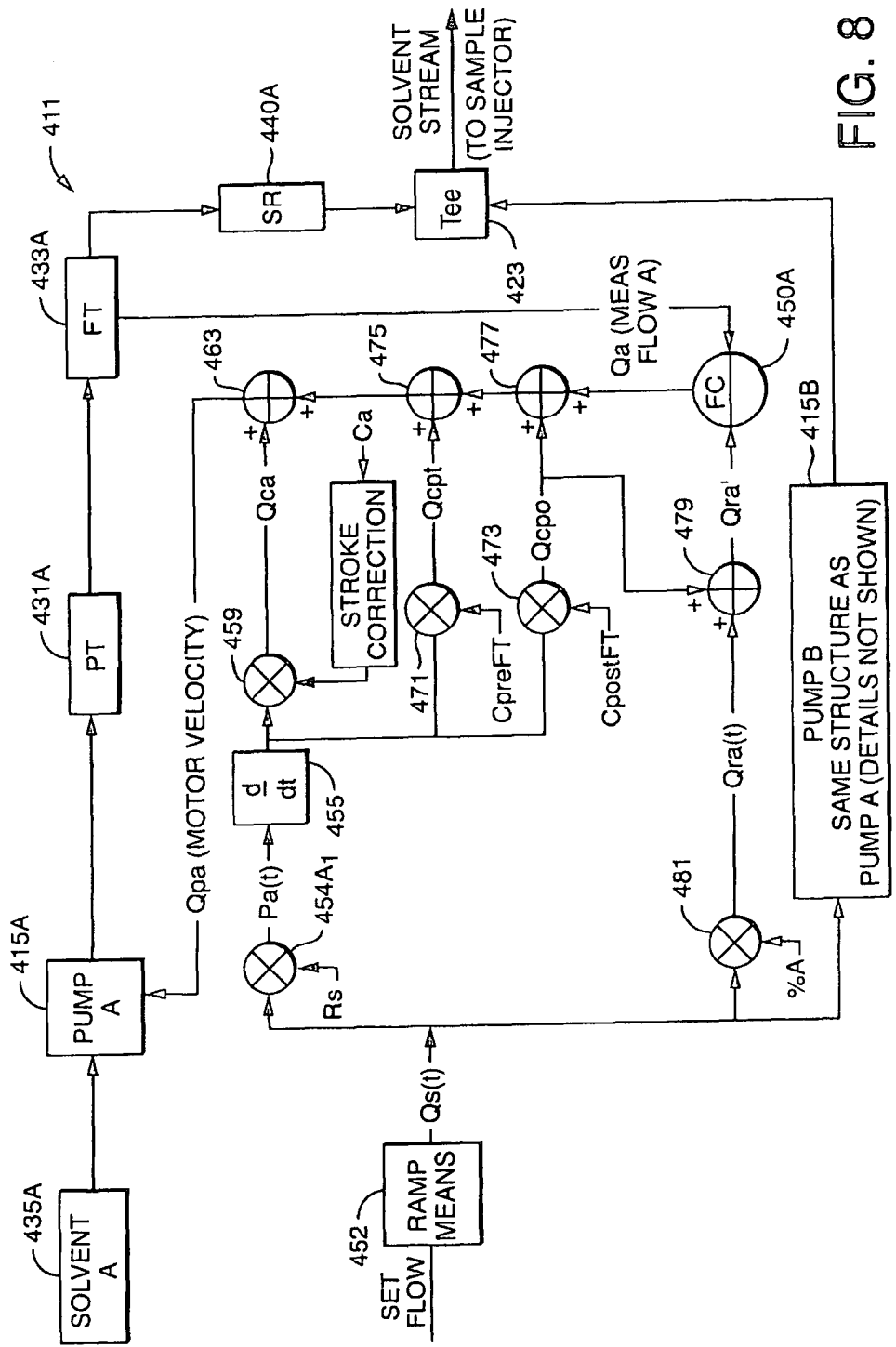
FIG. 8 is another more detailed version of an LC instrument shown to more particularly illustrate particular components of a feed forward signal in accordance with the subject technology.
Figure 9:
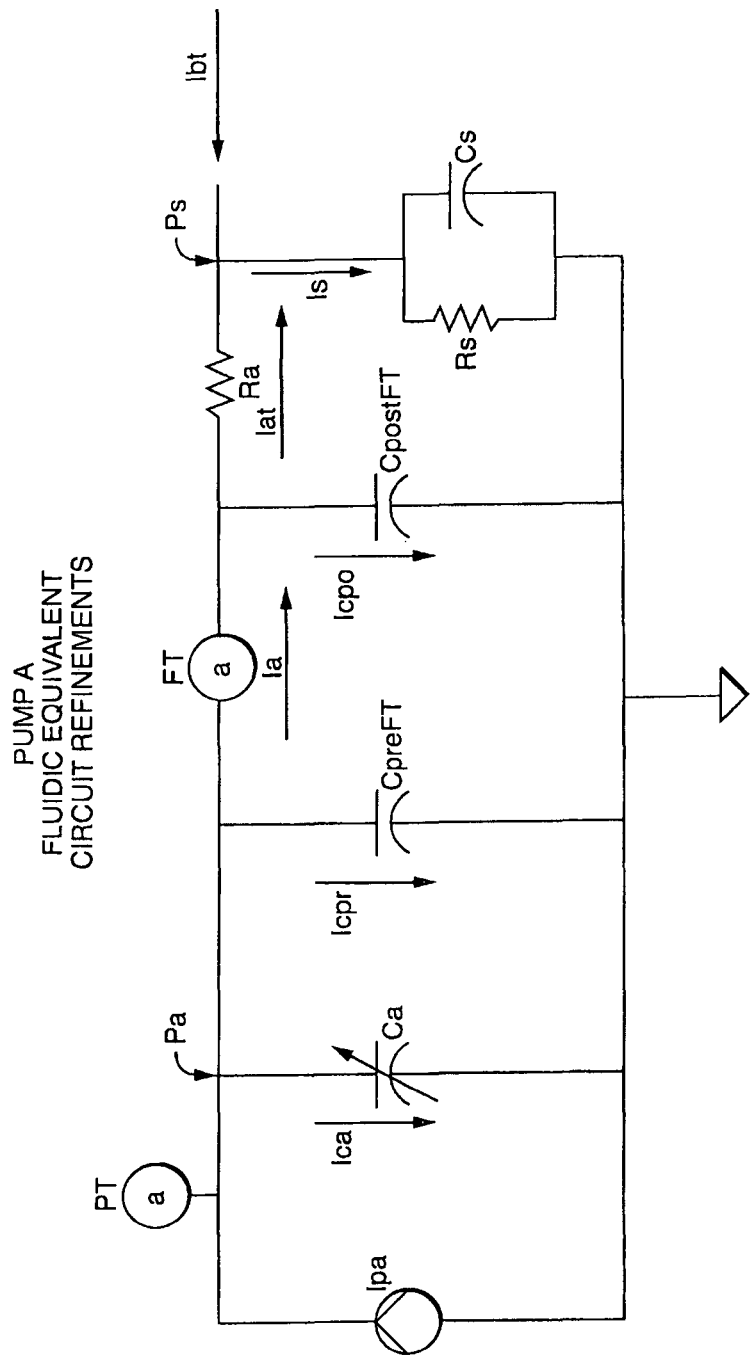
FIG. 9 is another electrical circuit analog to an LC instrument of having a system or load flow Is to provide energy or charge Cs to the load in accordance with the subject technology.

FIG. 8 is another more detailed version of an LC instrument shown to more particularly illustrate particular components of a refined feed forward signal in accordance with the subject technology. FIG. 9 is another electrical circuit analog to an LC instrument of having a system or load flow Is to provide energy or charge Cs to the load in accordance with FIG. 8. For simplicity, FIG. 8 depicts only the fluid stream or leg of the pump 415A into the mixing tee 423, and all explanations of the fluid refinements described here also apply symmetrically across the mixing tee 423 to the leg of pump 415B.

A first refinement of the feed-forward control involves consideration of the changing volume of the pump 415A and resultant capacitance Ca during the delivery stroke. As the stroke traverses from bottom dead center to top dead center of the pump 415A, the effective pump capacitance Ca varies with a net change proportional to the ratio of the stroke volume to the sum of the stroke and fixed captive volumes.

Since the stroke volume can be significant, Ca is a time-varying parameter, as shown in FIG. 9, and can be corrected during feed-forward control. A proper correction is made by monitoring the plunger travel position and making the appropriate change to the varying captive volume Vo before multiplying by the solvent compressibility factor β. The plunger position is known by reading either the direct commanded motor position or by measuring a motor shaft encoder, linear position indicator and the like as provided. The correction to the time-varying value of Ca is depicted in FIG. 8 as stroke volume correction to Ca before multiplier 459.

A second refinement of the feed-forward control scheme involves consideration of the captive fluid volume of the in-line flow transducers and the related undesirable energy storage effects. In one embodiment, each flow transducer 433A, 433B is constructed from a cylindrical tube (not shown) with a captive volume of just over 2 μL. The measuring elements are arranged symmetrically along the length of the tube, roughly splitting the captive volume evenly upstream and downstream from a mid point, which is the virtual node at which the flow measurement is made. The energy storage effects caused by these captive volume elements can be represented as two shunt capacitances, CpreFT and CpostFT in FIG. 8, flanking the transducer 433A.

FIG. 9 incorporates the upstream and downstream capacitances CpreFT and CpostFT that flank the flow transducer. In FIG. 9, FTa represents an ideal virtual transducer that produces a measured flow signal at a vanishingly small point centered between the flanking capacitances of the physical device. The transducer capacitances CpreFT and Cpost give rise to the corresponding shunt currents, Icpr and Icpo, whenever the pump 415A pressure at node Pa changes. The refinements made to the feed-forward control scheme account for these additional shut currents as shown in FIG. 9 entering multipliers 471, 473 and passing into summing junctions 475, 477. These feed-forward flows compensate the transducer charging currents needed to satisfy the commanded pressure ramp at the output of multiplier 454A1. For practical purposes, the upstream transducer capacitance, CpreFT, is subsumed by the much larger pump cylinder volume or capacitance Ca, so the effect of the shunt current Icpr on the measured flow is negligible. Thus, the flow through the transducer substantially consists of the flow of the pump 415A Iat into the mixing tee 423 and the charging flow Icpo, due to the down-stream capacitance of the flow transducer 433A. In practical applications, the capacitance CpostFT that gives rise to the charging flow Icpo accounts for any captive volume of the series restrictor 440A, which can be minimized by using capillary tubing. With this model, the flow transducer 433A produces a measurement error of the desired control flow, Iat, whenever the pressure Pa of the pump 415A changes. The error term is the post transducer charging flow Icpo.

A third refinement is made to the control scheme by correcting the flow transducer measured flow error at the feedback controller 450A as shown in FIG. 8 by summing junction 479, which sums the feed-forward calculated value Icpo into the setpoint of the flow controller 450A. To see how the correction is accomplished, the flow controller 450A responds to an internal error detector signal, set point minus measurement, which is expressed as (Qra'−Qa). The set point term Qra' is the actual driving set point Qra and the computed error term of the flow measurement Icpo. However, the flow transducer measurement responds to the sum of Iat and Icpo. Thus, the flow error term is cancelled across the flow controller's error signal, producing the desired error signal (Qra−Qat).

Figure 10:
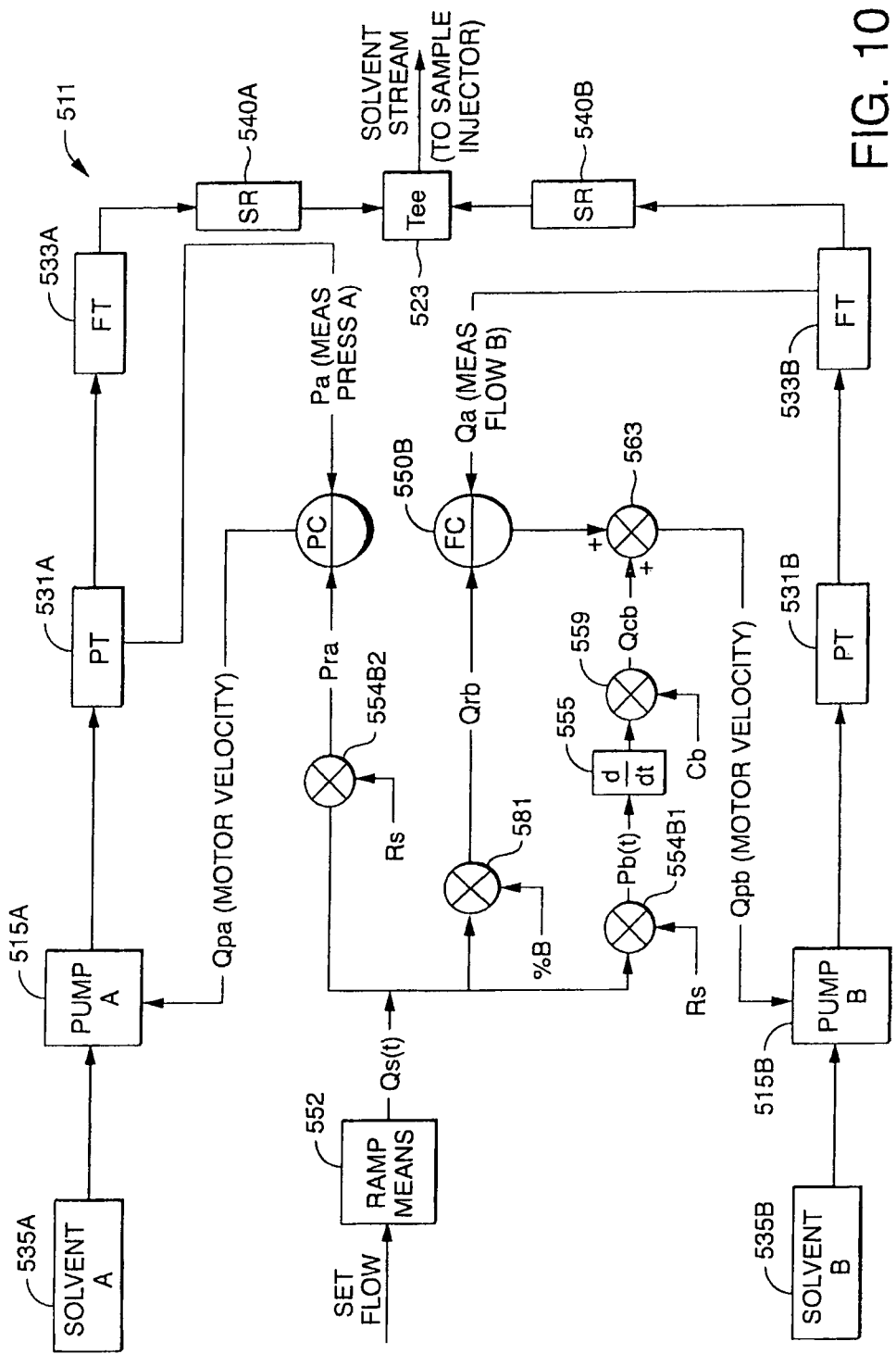
FIG. 10 is still another more detailed version of an LC instrument shown to more particularly illustrate a hybrid approach using a feed forward signal in accordance with the subject technology.

Referring to FIG. 10, still another more detailed version of an LC instrument shown to more particularly illustrate a hybrid approach using a feed forward signal in accordance with the subject technology. The control scheme shown in FIG. 10 can also be referred to as a hybrid pressure and flow control strategy or hybrid scheme. The hybrid scheme addresses the compressibility elements downstream of the mixing tee 523. In one embodiment, the downstream elements comprise user configurable components, making characterization by the control strategy impractical if possible at all. Such components include the injector sample loop and trapping columns, which are offered in various volume sizes. These components represent a lumped system capacitance attached to the outlet tee 523 and are represented in the fluidic models of FIGS. 6 and 8 as Cs, which appears in parallel with the very restrictive system resistance Rs of the analytical column (not shown). As noted above, using feed forward compensation can solve the composition control problems up to the mixing tee 523 that plague a feedback-only control strategy. However, when a large-volume component such as a sample loop and/or trapping column is added downstream of the mixing tee 523, the downstream capacitance Cs presents a very large charging flow demand to one or both of the flow controllers, depending on the mix ratio, while the flow ramps are in progress. Due to the magnitude of Cs, the system charging flow is much greater than the ramped bulk flow to the system and can easily exceed the flow range capability of the flow transducers 533A, 533B. The extra flow of Cs forces the flow transducers 533A, 533B to go open loop, resulting in a loss of composition control.

With the hybrid scheme, the control strategy for one of the flow legs into the mixing tee 523 is changed from flow control to pressure control, for example the leg of the pump 515A. The other leg, having the pump 515B, operates in flow control mode, with feed forward correction and all the refinements described earlier. In practice, the choice leg to use under flow control is the one handling the smallest contribution to the bulk flow, which is typically the organic pump 515B. Such is the state of the flow when starting and stopping the gradient or analytical run. During flow ramping with the hybrid scheme, the organic pump 515B under flow control with feed-forward compensation of compressibility, maintains the required stiffness under essentially a zero-flow condition to prevent sloshing of liquid across the mixing tee 523. Meanwhile, due to the complimentary nature of the two pump flows into the mixing tee 523, the aqueous pump 515A, under pressure control, supplies all the necessary charging flows, both up steam of the flow transducer 533A, and the charging flows downstream of the mixing tee 523. The complimentary pressure and flow mode of the hybrid approach prevents the feed back controller 550B of the flow-controlled leg from going open loop, while the pressure-controlled leg supplies the energy down stream of the mixing tee 523 needed to compress the rest of the system to follow the bulk flow ramp. With pressure mode incorporated into the control scheme, the flow-controlled leg of the pump 515B is prevented from going open loop and is able to keep up with its contribution to the bulk flow of the system, thus maintaining correct composition control into the system. In another embodiment, the hybrid scheme can incorporate the feed-forward correction elements 459, 463, 471, 473, 475, 477 shown in FIG. 9 into the output command signal of the pressure controller leg of the pump 515A of FIG. 10 to further provide enhanced error prevention and correction.

Performing Gradient Embodiments

Figure 11:
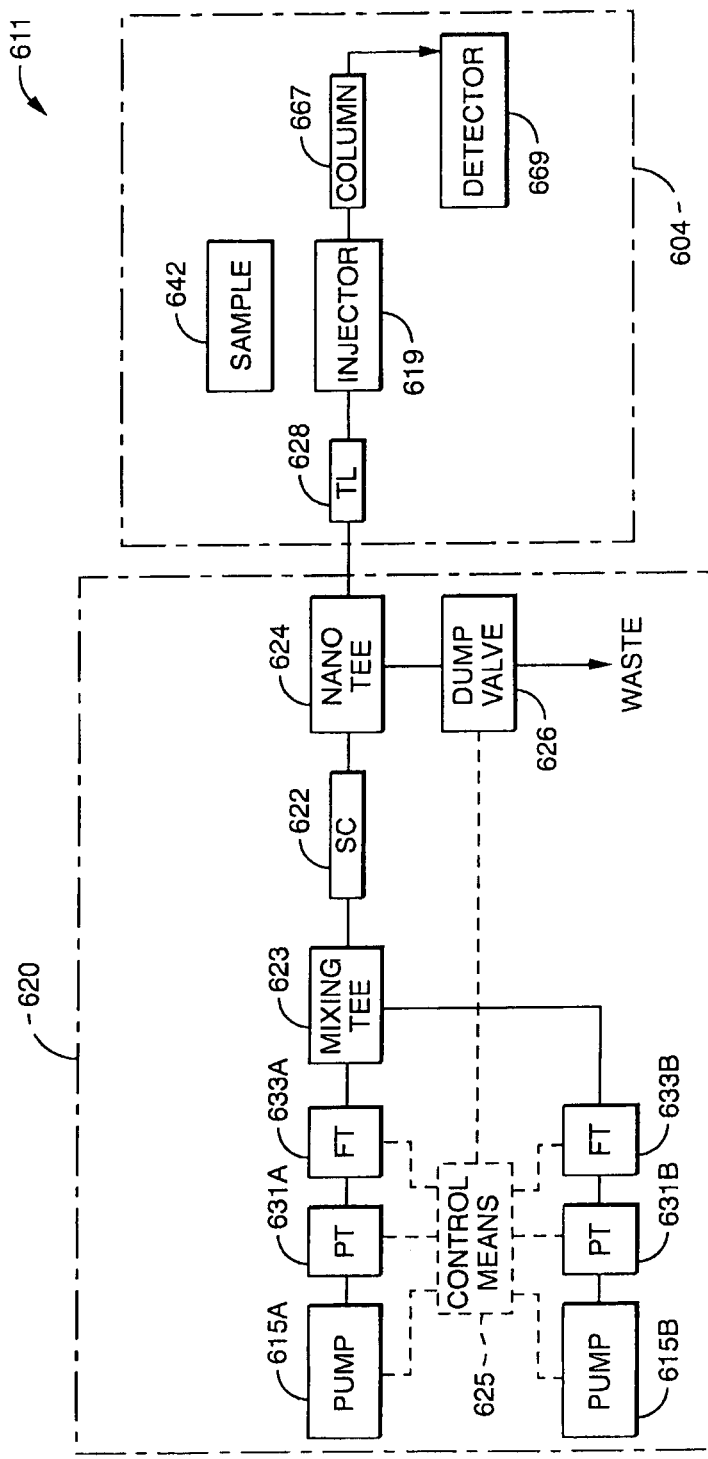
FIG. 11 is a somewhat schematic block diagram illustrating a direct-flow nano-scale HPLC system using a solvent delivery subsystem that preforms gradients in accordance with the subject technology.

Referring to FIG. 11, another direct-flow nano-scale HPLC instrument 611 in accordance with the subject technology is shown. As will be appreciated by those of ordinary skill in the pertinent art, the instrument 611 utilizes similar principles to the instruments described above. Accordingly, like reference numerals preceded by the numeral "6" are used to indicate like elements whenever possible. A primary difference of the instrument 611 in comparison to the instruments above is the use of a storage capillary 622 to retain a preformed gradient. As would be appreciated by those of ordinary skill in the art, the subject methods and systems described herein can be used together, separately and in any combination to achieve the desired performance. Similar to above, the HPLC instrument 611 has two major components, a binary solvent gradient delivery subsystem 620 and an analytical subsystem 604. The solvent delivery subsystem 620 forms and provides a gradient to the analytical subsystem 604, which generates a chromatogram thereon. It is envisioned that the solvent delivery subsystem 620 could be adapted to many alternative analytical designs to provide the advantages of the subject technology. In brief overview, the solvent delivery subsystem 620 performs relatively low pressure mixing of solvents A and B in one step to form a gradient and subsequent high pressure delivery of the gradient to the analytical subsystem 604 in a second step. These steps are orthogonal in that the first mixing step is independent and does not interfere with the second delivery step. The solvent delivery subsystem 620 is binary in that two pumps 615A, 615B are employed. Each pump 615A, 615B produces an output directed through an inline pressure transducer 631A, 631B and a flow transducer 633A, 633B, respectively. A controller 625 governs the operation of the pumps 615A, 615B and receives signals from the transducers 631A, 631B, 633A, 633B.

A mixing node or tee 623 combines the pump outputs to form the desired solvent mixture, which flows into a storage capillary 622 to form a gradient. Preferably, the mixing tee 623 is a T-shaped fitting and the storage capillary 622 is sized to minimize backpressure and dispersion. Downflow from the storage capillary 622, a nano-tee fitting 624 forms two outlets. One outlet of the nano-tee fitting 624 connects to the analytical subsystem 604 while the other outlet connects to a dump valve 626. The operation of the dump valve 626 is also governed by the controller 625 such that during forming the gradient in the storage capillary 622, the dump valve 626 is open to direct resident fluid to waste while both pumps 615A, 615B run. During delivery of the gradient to the analytical subsystem 604, only pump 615A runs and the other pump 615B is "offline". Preferably, the selection and arrangement of the components of the instrument 611 moves the outlet of the solvent delivery subsystem 620 from the outlet of the mixing tee 623 to the outlet of the nano-tee fitting 624. The dump valve 626 is preferably a pin valve. But instead of a pin valve, you could use a ball valve, a gate valve, a globe valve, a butterfly valve and the like.

The analytical subsystem 604 includes a transport line 628, such as a short capillary tube, that connects the outlet of the solvent delivery subsystem 620 to a sample injector 619. The sample injector 619 introduces one or more analyte samples, stored in sample retainer 642, into the gradient or fluid stream. Once the analyte is present, the fluid stream is directed to a column 667 for analysis. In the column 667, the analytes are isolated, separated and directed to a detector 669. Preferably, the detector 669 is any type, such as a mass spectrometer, an ultra-violet detector and the like, that is suitable for the particular application. Based upon the readings of the detector 669, a chromatogram is generated. Preferably, pump 615A is an independent high-pressure pump that sources one of two mobile-phase solvents (e.g., an aqueous solvent) from a reservoir supply (not shown) to the mixing tee 623. Similar to above, the solvent flow at the outlet of the aqueous pump 615A is read by the inline pressure transducer 631A to provide a measurement of the instrument operating pressure. The flow transducer 633A provides a direct nano-flow measurement of the aqueous solvent upon entry into the mixing tee 623. Each of these signals is passed to the controller 625 for closed-loop control of the aqueous pump 615A. Thus, the controller 625 is able to maintain accurate flow delivery upstream from the flow transducer 633A despite the presence of large parasitic flow leakages due to high-pressure seals, check valves of the aqueous pump 615A and similar issues well-known to those of ordinary skill in the pertinent art.

Similarly, pump 615B is another independent high-pressure pump feeding the pressure transducer 631B and flow transducer 633B. However, in contrast, pump 615B sources a complementary mobile-phase solvent (e.g., an organic solvent) from a reservoir supply (not shown) to the mixing tee 623. Because the signals of the pressure transducer 631B and flow transducer 633B are also fed to the controller 625, complete closed-loop control is possible. The controller 625 establishes a desired user-set bulk flow to the analytical subsystem 604 as well as the compositional mix ratio of the two solvents by regulating the delivery flow of each pump 615A, 615B into the mixing tee 623. In one embodiment, the conduits from the flow transducers 633A, 633B are capillary restrictors to provide passive fluidic decoupling between the two pumps 615A, 615B to stabilize the inherent interactions of the two flow control loops across the mixing tee 623. In another embodiment, the capillary restrictors are provided upstream from the flow transducers 633A, 633B. In either case or when both are used, feedback instability from the two pumps 615A, 615B is avoided as well as cross-flow and/or back-flow contamination.

Gradient Formation and Delivery

Figure 12:
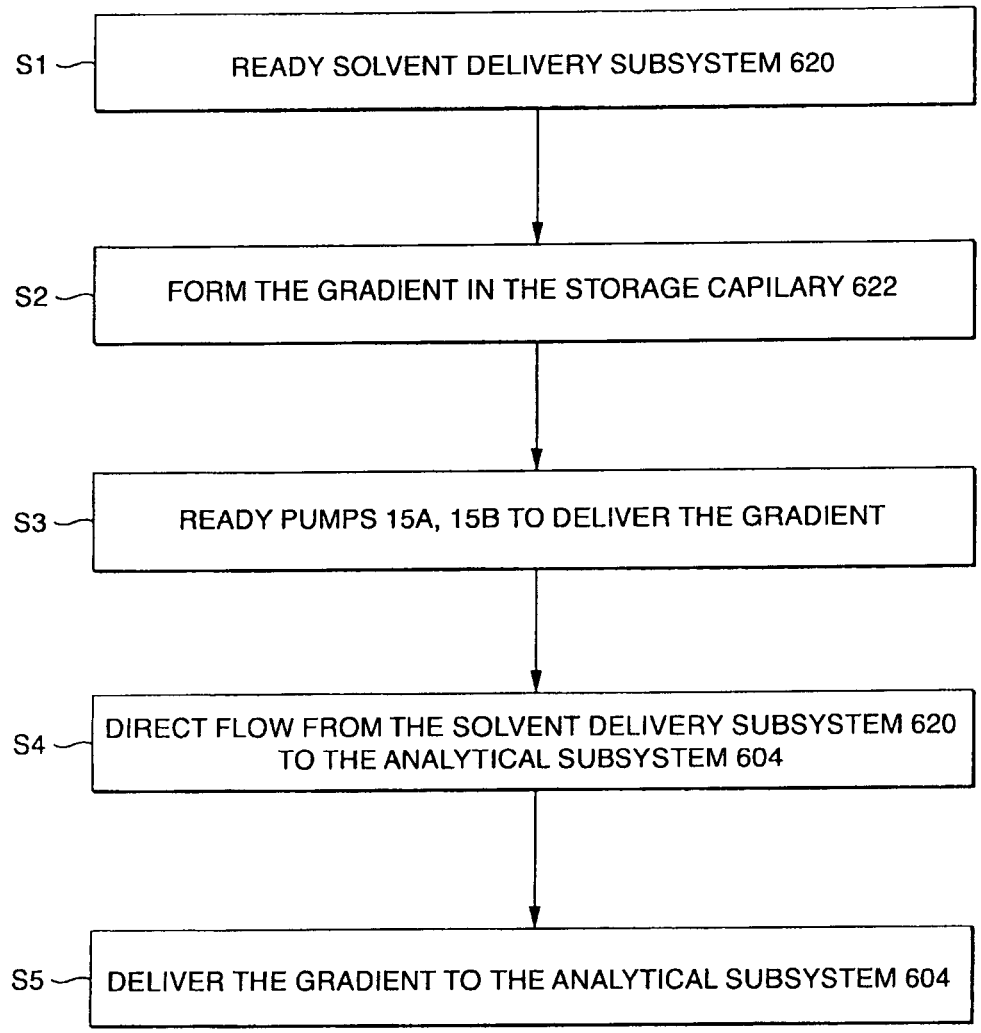
FIG. 12 is a flow diagram of a process for forming and delivering a gradient in the system of FIG. 1 in accordance with the subject technology.

Referring now to FIG. 12, a process for operating the solvent delivery subsystem 620 to provide a gradient to the analytical subsystem 604 is shown as a flow diagram. At step S1, prior to gradient formation, the controller 625 readies the solvent delivery subsystem 620 by opening the dump valve 626 to direct the old resident fluid (e.g., 100% aqueous solvent) inside the storage capillary 622 to waste. It is envisioned that any suitable conduit, tube or microfluidic structure now know or later developed could be used to perform the function of the storage capillary 622. Formation of the gradient with the storage capillary 622 essentially vented to atmosphere accomplishes three functions: 1) the formation back pressure is accurately controlled by the geometry of the storage capillary 622, independent of the column 667 or other connected consumables; 2) the fluid in the storage capillary 622 is purged to waste to prevent upsetting the equilibrium state of the column 667 between injection runs; and 3) any leading or trailing compositional aberrations bracketing the formed gradient, due to starting and stopping the flow during formation, are directed away from the primary fluid stream of the instrument 611, i.e., away from the analytical subsystem 604 and the column 667 therein. At step S2, the gradient is formed in the storage capillary 622 by operating the pumps 615A, 615B at low pressure (e.g., 100 psi) and higher flow rate (e.g., ten to twenty times the normal chromatographic flow rate). Preferably, the storage capillary 622 receives the gradient in a FIFO fashion. Once the gradient is formed in the storage capillary 622, delivery to the analytical subsystem 604 can occur later, at high pressure and at the normal chromatographic flow rate. The geometry of the storage capillary 622 is sized by length and inner diameter to achieve the necessary storage volume capacity for the gradient and to minimize the formation of backpressure and gradient dispersion. In addition to the entire gradient, the volume capacity of the storage capillary 622 is preferably large enough to accommodate the additional overhead of transport volume necessary to move the gradient from the storage capillary 22 to the column 667.

Still referring to FIG. 12, at step S3, the organic pump 615B is taken offline to ready for delivering the gradient. Thus, the organic pump 615B does not participate in gradient delivery to the analytical subsystem 604. In a preferred embodiment, the organic pump 615B is taken offline by the controller 625 by maintaining closed-loop flow control of the organic pump 615B with a reference flow setting of zero. In another embodiment, the organic pump 615B is taken offline by employing an isolation valve (not shown) upstream from and adjacent to the mixing tee 623.

At step S4, the controller 625 closes the dump valve 626 to direct flow of the formed gradient to the analytical subsystem 604. As a result, the aqueous pump 615A, operating under closed-loop flow control, is solely used as the prime mover to push the gradient out of the storage capillary 622 for delivery at step S5.

Flow Control for Multiple Columns

For applications that require changing the operational flow rate for a particular choice of column during an injection run, e.g., sample trapping and 2-D chromatography, the flow rate is started and stopped between selection of each column. The solvent delivery subsystem 620 of FIG. 11 is well-suited to provide varying gradients in such LC systems despite relatively large cylinder volumes of the pumps 615A, 615B and the nano-scale of flow delivery to the columns. In one embodiment, the controller 625 resets the pumps 615A, 615B with the dump valve 626 open to waste and waits for the solvent delivery subsystem 620 to achieve steady state flow. Although effective, this operation can be undesirably time consuming because of the relatively large volume change of stored energy required to compress the fluid stream up to the to operational back pressure.

For example, the compressibility constant (i.e., change in volume per change in pressure) of the aqueous pump 615A is preferably about 0.5 nL/psi. The time required to reach a steady-state pressure of about 9,000 psi at a flow rate of 300 nL/min to a particular capillary column [e.g., 75 μm ID×250 mm×1.7 μm particles] would be about 15 minutes as shown in the calculation below.

$$\Delta V = C \cdot \Delta P = 0.0005 \text{ uL/psi} * 9,000 \text{ psi} = 4.5 \text{ uL}$$

$$T = \Delta V/q = 4.5 \text{ uL}/0.300 \text{ uL/min} = 15 \text{ min}$$

Figure 13:
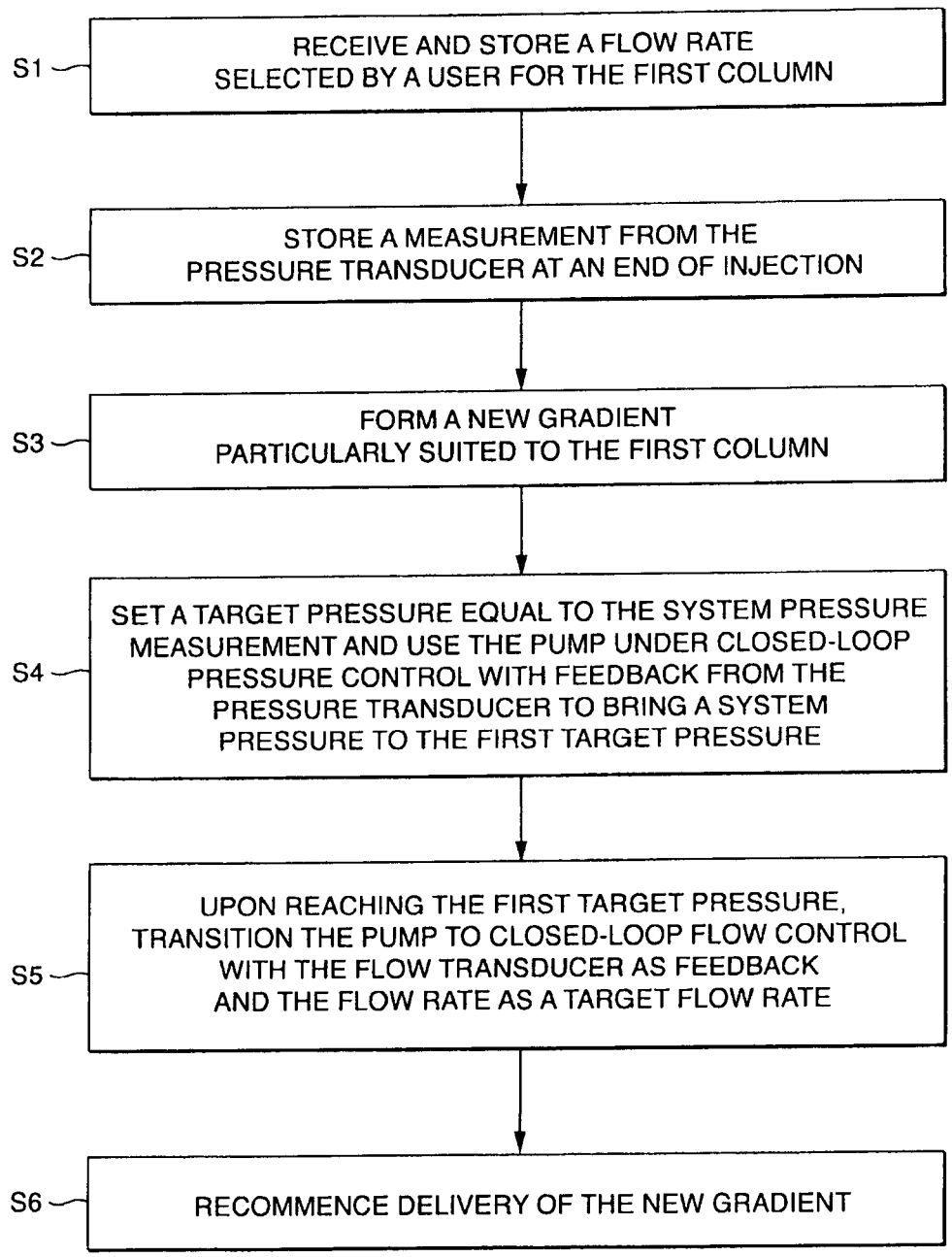
FIG. 13 is another flow diagram of a process for avoiding a slow flow startup when performing a series of injection runs using different columns in accordance with the subject technology.

Referring now to FIG. 13, a process is shown that avoids a slow flow startup when performing a series of injection runs by a solvent delivery subsystem to a LC system (not shown) having multiple columns. Although not shown separately, this solvent delivery subsystem can be exactly as represented in FIG. 11. Thus for clarity, the reference to the solvent delivery subsystem 620 of FIG. 11 is again utilized. In brief overview, the solvent delivery subsystem 620 commences flow delivery under pressure control to rapidly compress the system pressure to a former steady state flow condition from the previous run, then transitions to flow control.

The process of FIG. 13 commences from the end of an injection run when the column is to be re-equilibrated to the starting conditions for the next run. At step S1 of FIG. 13, the controller 625 receives and stores a flow rate selected by a user for the next column to be used. At step S2, the controller 625 stores the system pressure measurements from the pressure transducers 633 as was desired for the previous column injection. At step S3, the flow is stopped, and a new gradient is formed, as described above with respect to FIG. 2. To commence flow delivery, the controller 625 configures the aqueous pump 615A to operate under closed-loop pressure control, using the pressure transducer 633A as feedback.

At step S4, the controller 625 sets the reference set point (e.g., the target pressure) to the system pressure measurement stored from the previous run. Then, the aqueous pump 615A is run to attain the reference set point. Once the system pressure reaches the reference set point, i.e., compresses back to the steady state pressure, the process of FIG. 13 proceeds to step S5.

At step S5, the controller 625 transitions the aqueous pump 615A back to closed-loop flow control, using the flow transducer 633A as feedback, and sets the reference set point to the user-set elution flow rate received at step S1. Upon reaching the desired elution flow rate, the process proceeds to step S6 in which delivery of the new gradient occurs. Preferably, the aqueous pump 615A, operating under closed-loop flow control, is solely used as the prime mover to push the gradient out of the storage capillary 622 for delivery.

Further variations to the design shown in FIG. 11 are also well within the scope of the subject technology. For example, without limitation, the storage capillary 622, the nano-tee fitting 624, and the dump valve 626 are shown before the injector 619 in FIG. 11. To minimize the gradient transport delay, these elements 622, 624, 626 could be located as close as possible to the injector 619. As a result, the transport line or element 628 can be eliminated and replaced by the storage capillary 622. Moving the storage capillary 622 in closer proximity to the sample injector 619 and column 667 also presents the opportunity to co-locate the storage capillary 622 with the column 667, which is often placed in a thermally-managed compartment. Such placement of the storage capillary 622 favorably isolates the storage capillary 622 from external temperature changes, enhancing retention-time reproducibility.

For another example, the subject technology can readily be adapted to WATERS® nanoACQUITY HPLC™ System, available from Waters Corporation of Milford, Mass., with the addition of a storage capillary and a dumping valve. In these instruments, the operational pressure is extended from 10,000 to a pressure rating of 15,000 psi or beyond, while the operational delivery flow rate is capable of being about 10 nL/min. Further, the WATERS® nanoACQUITY HPLC™ System can provide the variable flow/peak parking feature for enhanced sensitivity as discussed in more detail below and the feed forward compensation discussed above.

TRAPPING EMBODIMENTS

The subject technology is also advantageously applied to trapping applications that use short trapping columns (i.e., high captive volume applications) in series with very restrictive columns. In such circumstances, the stopping of flow is characterized by a long time interval in which the pressure finally subsides to near zero. The long time interval is due to the very large effective time constant of the trapping system created by the highly capacitive trapping column (i.e., the stored energy of compression) and the large restriction of the analytical column (i.e., the limited flow). The effective time constant can be many tens of minutes. To overcome this long time constant in trapping applications, the principles of the subject solvent delivery subsystems can be utilized. Further, by efficiently forming the gradient, usage of and wear upon the typical trapping components, such as valves, can be minimized to extend the life thereof.

Figure 14:
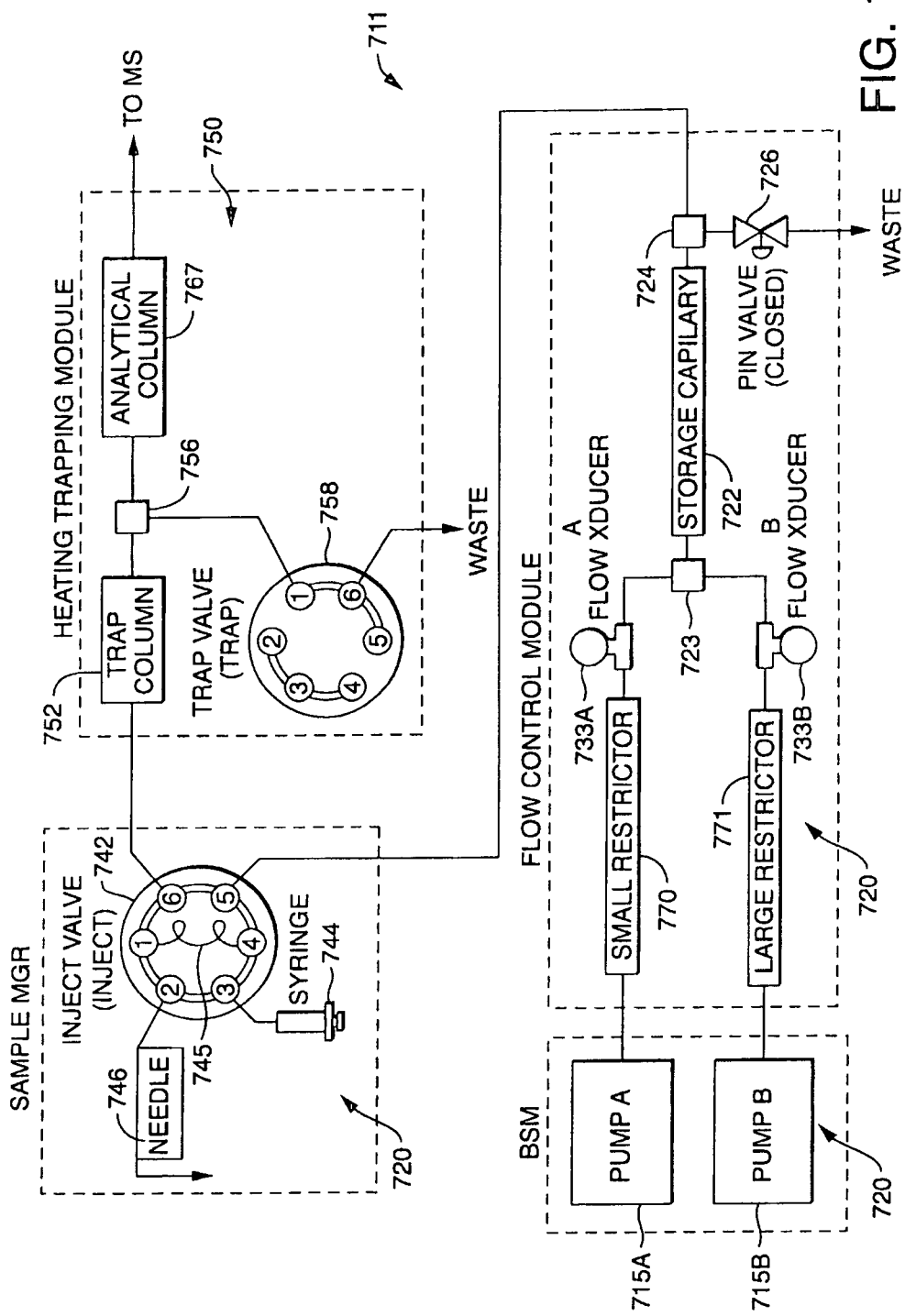
FIG. 14 is a somewhat schematic block diagram illustrating a direct-flow nano-scale trapping system using a solvent delivery subsystem in accordance with the subject technology.

Referring now to FIG. 14, a solvent delivery system 720 is shown in use in a trapping application system 711. As will be appreciated by those of ordinary skill in the pertinent art, the system 711 utilizes a similar solvent delivery subsystem 720 as shown in FIG. 11. Accordingly, like reference numerals preceded by the numeral "7" are used to indicate like elements whenever possible. In the system 711, the operations of sample loading, sample trapping and gradient formation are preferably serialized.

The system 711 includes a sample manager 720 connected to a heating trapping module 704. The sample manager 720 includes an inject or load valve 742 connected to the solvent delivery subsystem 720 and the heating trapping module 750. A syringe 744 and needle 746 are also connected to the inject valve 742. The heating trapping module 750 has a trap column 752 in series with an analytical column 767, the trap column 752 being connected to the inject valve 742. A tee fitting 756, intermediate the trap column 752 and analytical column 767, connects to a trap valve 758.

For clarity, it is noted that pressure transducers are not shown in FIG. 14. The pressure transducers are present as an integral component of the pumps 715A, 715B. However, a small restrictor 770 is shown connected immediately upstream from the flow transducer 733A and a large restrictor 771 is shown connected immediately upstream from the flow transducer 733B, whereas such restrictors are preferably present but omitted in other embodiments herein. The restrictors 770, 771 serve to attenuate the potential interaction between the pumps 715A, 715B because of the mutual connection to the mixing tee 723. In effect, the restrictors 770, 771 minimize the backflow between the pumps 715A, 715B across the mixing tee 723. As the pump 715A acts as the primary mover and moves the most viscous liquid (e.g., water), the associated restrictor 770 is relatively smaller. In a preferred embodiment, the small restrictor 770 is approximately 0.025 cm inner diameter×20 cm long and the large restrictor 771 is approximately 0.025 cm inner diameter×45 cm long. In another preferred embodiment, the small restrictor 770 is approximately 25 μm I.D. by 20 cm and the large restrictor 771 is approximately 25 μm I.D. by 150 cm. While the restrictors may be different, the restrictors may also have the same value and dimensions.

To load a sample, the needle 746 is placed in the sample in a well-known manner. The syringe 744 provides suction to draw the sample through the needle 746 into the inject valve 742, which is set so that the flow passes from point 3 to point 4 to point 1 to point 2 of the inject valve 742 to the needle 746. Upon completion, the sample is located in a loop 745 between points 4 and 1 of the inject valve 742. At this point, the sample is ready to be cleaned and concentrated by being put onto the trap column 752.

During sample trapping, exact control of the flow is not required but high flow is desirable in order to move the sample from the loop 745 to the trap column 752. Typically, the sample is capillary scale such as approximately 4 uL/min. In a preferred embodiment, the solvent delivery system 720 moves 5-15 uL/min for a period of 5 minutes to move the sample onto the trap column 752 at only 1,000 psi.

For sample trapping, the conditions of the heating trapping module 750 advantageously transition from high pressure/low flow to low pressure/high flow. To accomplish this, the solvent delivery subsystem 720 stops flow by rapidly decompressing the heating trapping module 750 under pressure-control mode. The controller (not shown) accomplishes the rapid decompression by reconfiguring the aqueous or driving pump 715A from flow control to pressure control mode, using the internal pressure transducer as feedback. Then, the controller sets the reference pressure set point to zero and commences operation of the pump 715A. Preferably, the organic pump 715B is similarly controlled. In another embodiment, the aqueous pump 715A alone runs during sample trapping.

Still referring to FIG. 14, when the system 711 runs pumps 715A, 715B, the pin valve 726 is closed to direct flow into the inject valve 742 at point 5. The inject valve 742 is set so flow passes from point 5 to point 4 to point 1 to exit at point 2 carrying the sample therewith. The flow then passes into the heating trapping module 750 with a trap valve 758 being open to waste at point 6. As a result, the flow is directed through the trap column 752 but thereafter passes through the tee fitting 756 to waste via point 1 to point 6 of the trap valve 758. As a result of this flow, the sample passes onto the trap column 752.

Next, the system 711 forms the gradient to be used in the elution run. The solvent delivery subsystem 720 is run as described above to form the gradient. In particular, the pin valve 726 is open to waste and the pumps 715A, 715B are run until the gradient is in the storage capillary 722. Preferably, this results in a system pressure between ambient and 300 psi but high flow.

To perform an elution run, the solvent delivery subsystem 720 has pump 715A run as described above to deliver the gradient. The gradient enters point 5 of the inject valve 742 and exits point 6 into the trap column 752. With the trap valve 758 effectively closing the path to waste, the flow passes through the tee fitting 756 and analytical column 767 to the mass spectroscopy system (not shown). Even though the organic pump 715B is not delivering flow during the elution run, the pump 715B also compresses while set to zero flow. Otherwise, the pump 715A would force flow across the mixing tee 723 resulting in contamination. Alternatively, the contamination could be allowed and, prior to subsequent gradient formation, the pumps 715A, 715B could be run to waste for cleansing.

Figure 15:
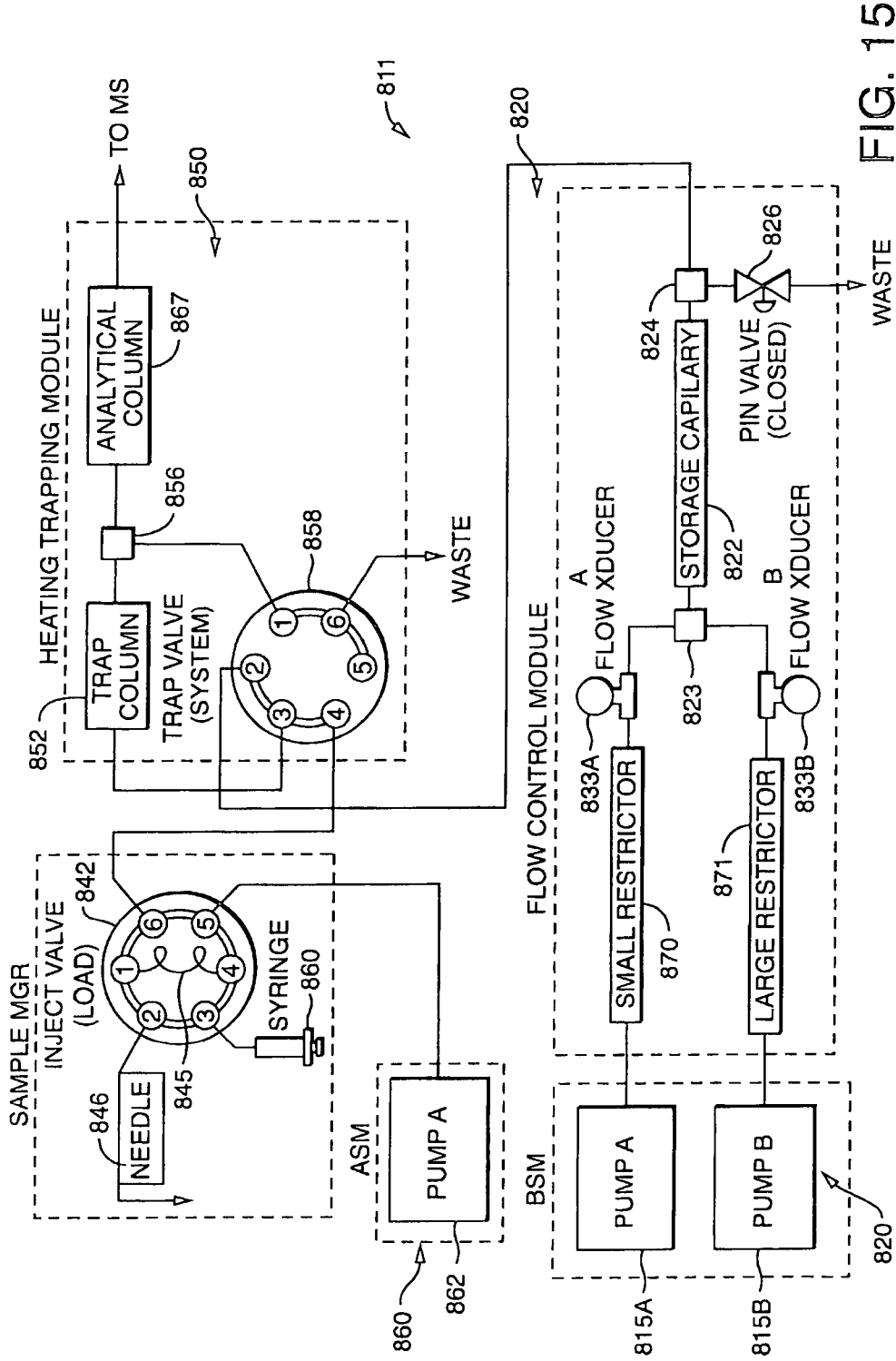
FIG. 15 is a somewhat schematic block diagram illustrating another direct-flow nano-scale trapping system using a solvent delivery subsystem with an additional pump in accordance with the subject technology.

Referring now to FIG. 15, another solvent delivery system 820 is shown in use in a trapping application system 811. As will be appreciated by those of ordinary skill in the pertinent art, the system 811 utilizes similar principles to the systems described above. Accordingly, like reference numerals with the first number of "8" are used to indicate like elements whenever possible. A primary difference of the system 811 is the addition of an auxiliary solvent manager (ASM) 860 and modified plumbing to accommodate the ASM 860. The system 811 allows for more parallelism between the operations of sample loading, sample trapping and gradient formation. Additionally, less flow interruption and a single composition trapping operation can be realized.

The ASM 860 has an additional pump 862 connected to point 5 of the inject valve 842. Rather than connecting to the trap column 852, the point 6 of the inject valve 842 connects to point 4 of the trap valve 858. The output of the solvent delivery subsystem 820 connects to point 2 of the trap valve 858 such that the trap column 852 can receive flow from the inject valve 842 or solvent delivery subsystem 820 as selected by the controller (not shown).

It is envisioned that the sample loading and the gradient formation can be performed simultaneously. By having the output of the solvent delivery subsystem 820 connected to the trap valve 858, the sample manager 440B is isolated such that these operations can occur simultaneously. Additionally, sample trapping and gradient formation can occur in parallel. While the gradient if formed as described above with respect to FIG. 14, the pump 862 pushes flow into the inject valve 842 at point 5 to point 4, through the loop 845 through point 1 to exit at point 6. The flow continues into the trap valve 858 at point 4 to exit point 3 into the trap column 852. Upon exiting the trap column 852, the flow moves to waste via tee 856 and again into the trap valve 858 at point 1 to exit at point 6.

During an elution run, the system 811 operates very similarly to that described above with the aqueous pump 815A being the primary mover of fluid while the organic pump 815B compresses but is set to zero flow. Consequently, the gradient moves from the storage capillary 822 into the trap valve 858 at point 3 to exit at point 2. From the trap valve 858, the flow passes through the trap column 852 into the analytical column 867 because the path to waste is closed.

The configuration of system 811 also advantageously allows for component optimization. For example, pump 862 typically runs at high flow, say 20 uL/min whereas the aqueous pump 815A may run at a fraction of a uL/min. Rather than trying to use a single transducer to cover this flow range, each pump 815A, 862 can have a flow transducer specifically tuned for the relevant range.

Peak Parking Embodiments

Figure 4:
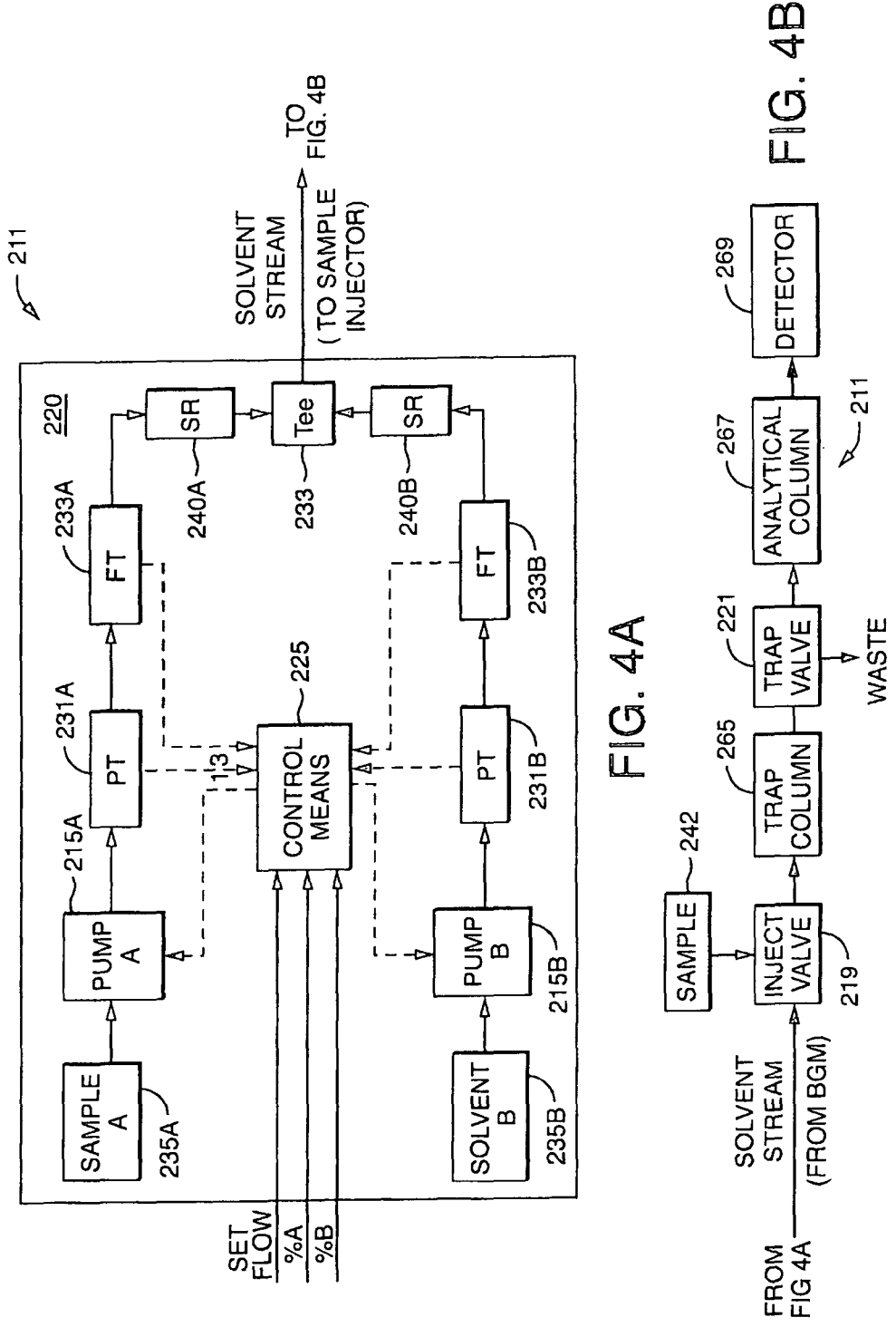
FIGS. 4A and 4B are a somewhat schematic block diagram illustrating a HPLC instrument using a solvent delivery subsystem that utilizes feed-forward principles in accordance with the subject technology, wherein matching instructions are present to illustrate how to properly connect FIGS. 4A and 4B.
Figure 16:
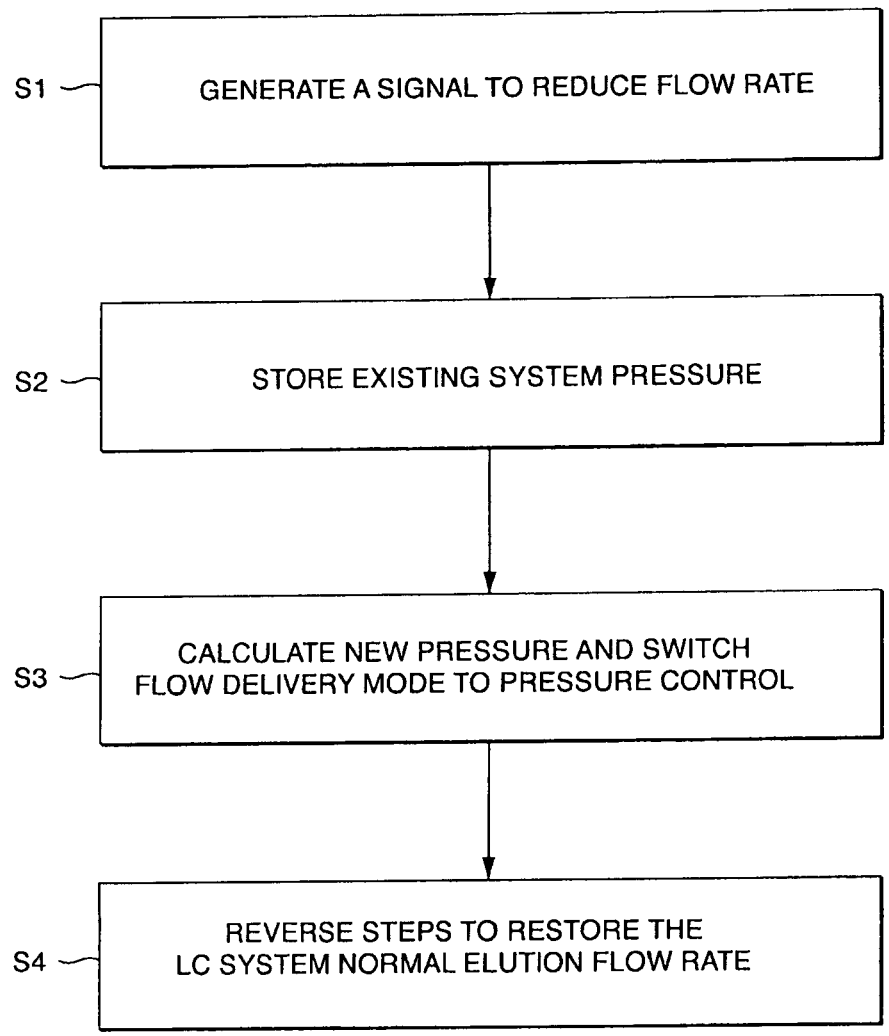
FIG. 16 is another flow diagram of a process for peak parking in accordance with the subject technology.

Referring now to FIG. 16, a process is shown that rapidly reduces the elution flow rate of the solvent delivery subsystem 620 to the analytical subsystem 604 of, for example, FIG. 11. FIG. 11 is referred to again for clarity and as the same components can be used to efficiently accomplish this peak parking. It is envisioned that the peak parking can also be performed with the configuration of many other fluidic chromatography systems, such as that shown in FIG. 4. In FIG. 11, only the delivery pump, typically 631A, would "ramp" to the new desired flow since that is the only pump responsible for fluid delivery when a gradient is being delivered to the analytical column 676. In the case of FIG. 4, both transducers 231AB, 233AB would be utilized to control the ramping procedure. At step S1 of FIG. 16, upon detection of a single elution peak of interest by the detector 669, the controller 625 receives a signal to "park" or reduce the bulk flow to the analytical subsystem 604. In one embodiment, the analytical subsystem 604 sends the park signal to the controller 625. At step S2, the controller 625 stores the existing system pressure measurement from the pressure transducers 631A, 631B.

At step S3, the controller 625 calculates a new reduced target pressure and switches from closed-loop flow control to closed-loop pressure control using the pressure transducers 631A, 631B.[2] Preferably, the controller 625 calculates the new reduced target pressure by assuming a linear 'Ohmic' fluidic load of the LC instrument 611 according to the following formula R=delivery pressure divided by delivery flow where R is a restrictive load. In other words, to determine the reduced pressure, the controller 625 targets the reduced pressure needed by the same ratio as the desired flow rate reduction. For example, consider a system delivering fluid at 300 nL/min at a system pressure of 9000 psi. This would correlate to a system load of 30 psi/(nL/min). If the target flow rate was 50 nL/min, then the target pressure for this system would be 1500 psi.

Depending on the duration of the peak park event, the controller 625 may transition back to flow control mode at the reduced flow setting, for more accurate and reproducible flow delivery. Operating in pressure mode gives the advantage of a faster decompression response time, since the flow transducers 633A, 633B have much less signal bandwidth compared to the pressure transducers 631A, 631B. As a result, the elution flow rate can be reduced by up to fifty times or even more.

At step S4, detection of the elution peak is completed and the controller 625 restores the flow back to the normal elution flow rate by reversing steps S1-S3, using the stored system pressure measurement as the new pressure target. The advantages of this approach over conventional high-pressure mixing schemes is that the problems associated with corruption of the gradient when compressibility energy is taken out or put back into the fluid stream are eliminated because the gradient is preformed and only a single fluid driving pump (e.g., the aqueous pump 615A) is used to affect the flow change.

Co-Locating a Gradient Storage

Device with Column Embodiments

Figure 17:
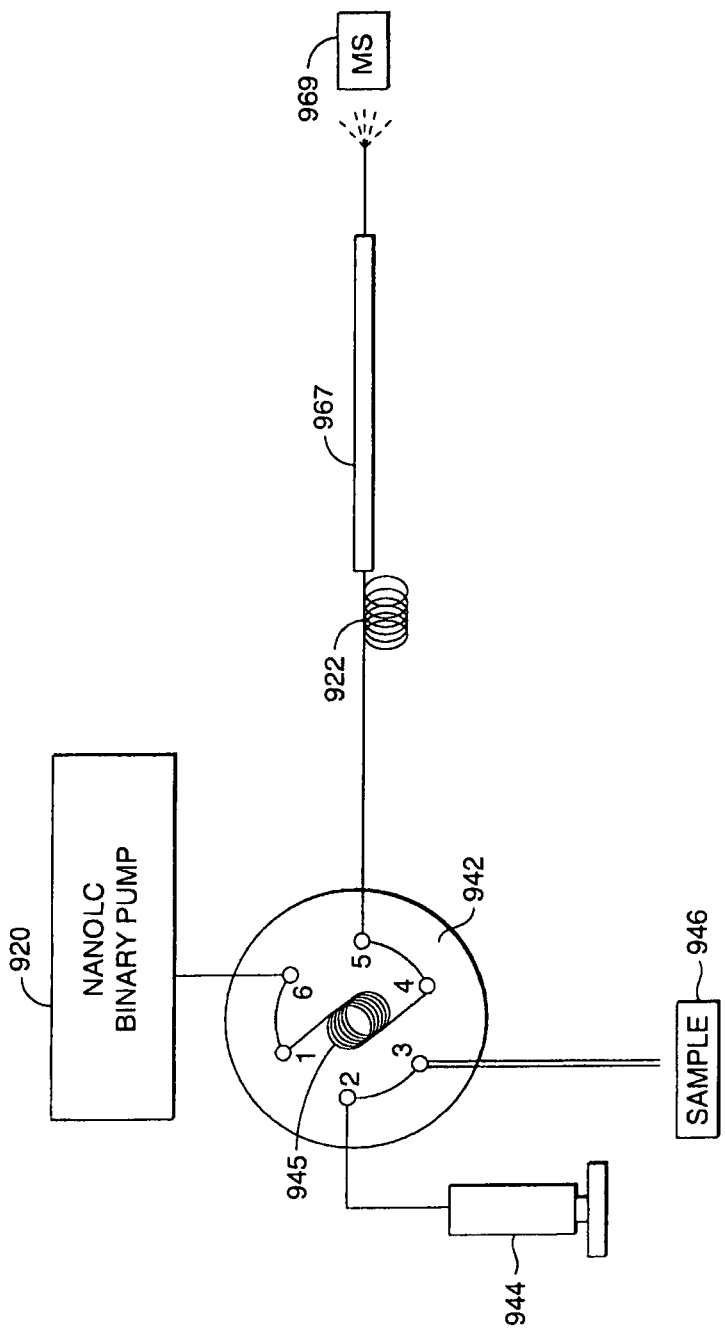
FIG. 17 is a somewhat schematic block diagram illustrating a LC instrument using a gradient storage device without a vent valve in accordance with the subject technology.
Figure 18:
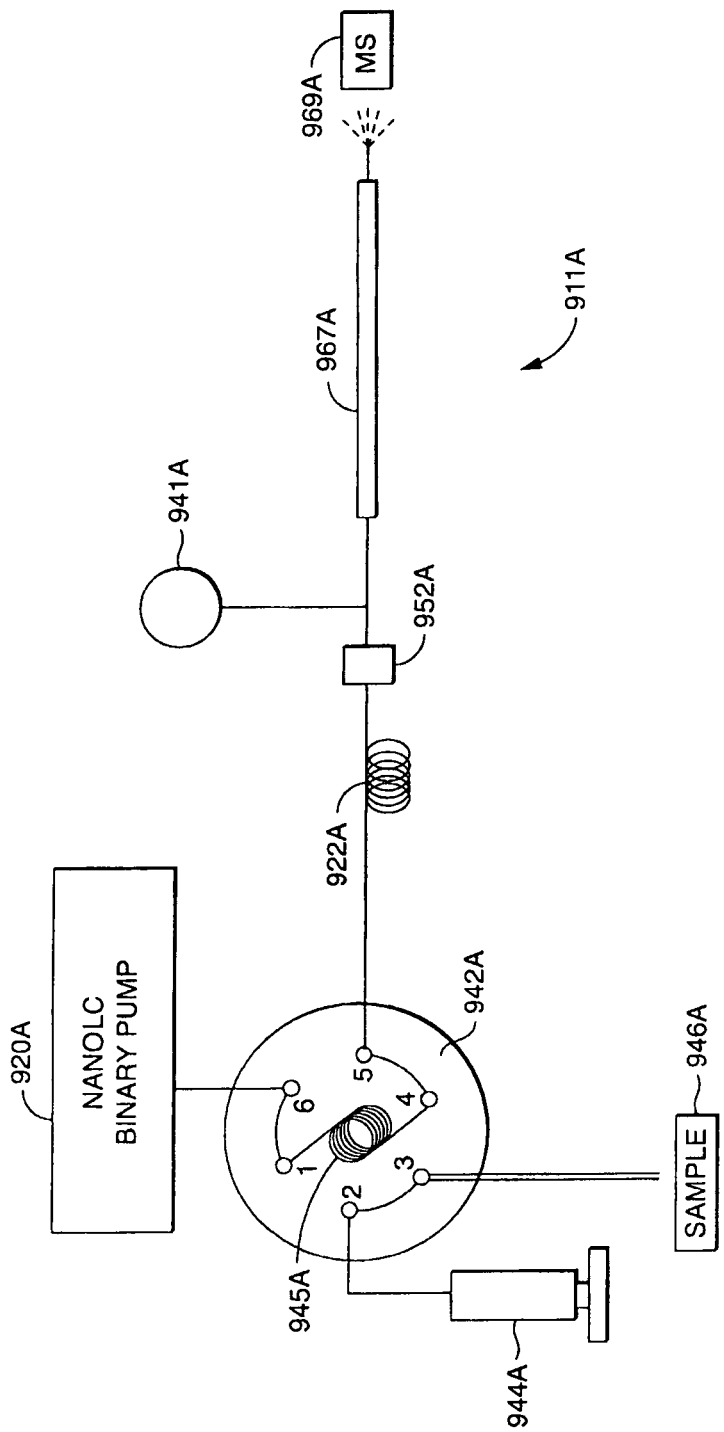
FIG. 18 is a somewhat schematic block diagram illustrating another LC instrument using a gradient storage device with a vent valve in accordance with the subject technology.
Figure 19:
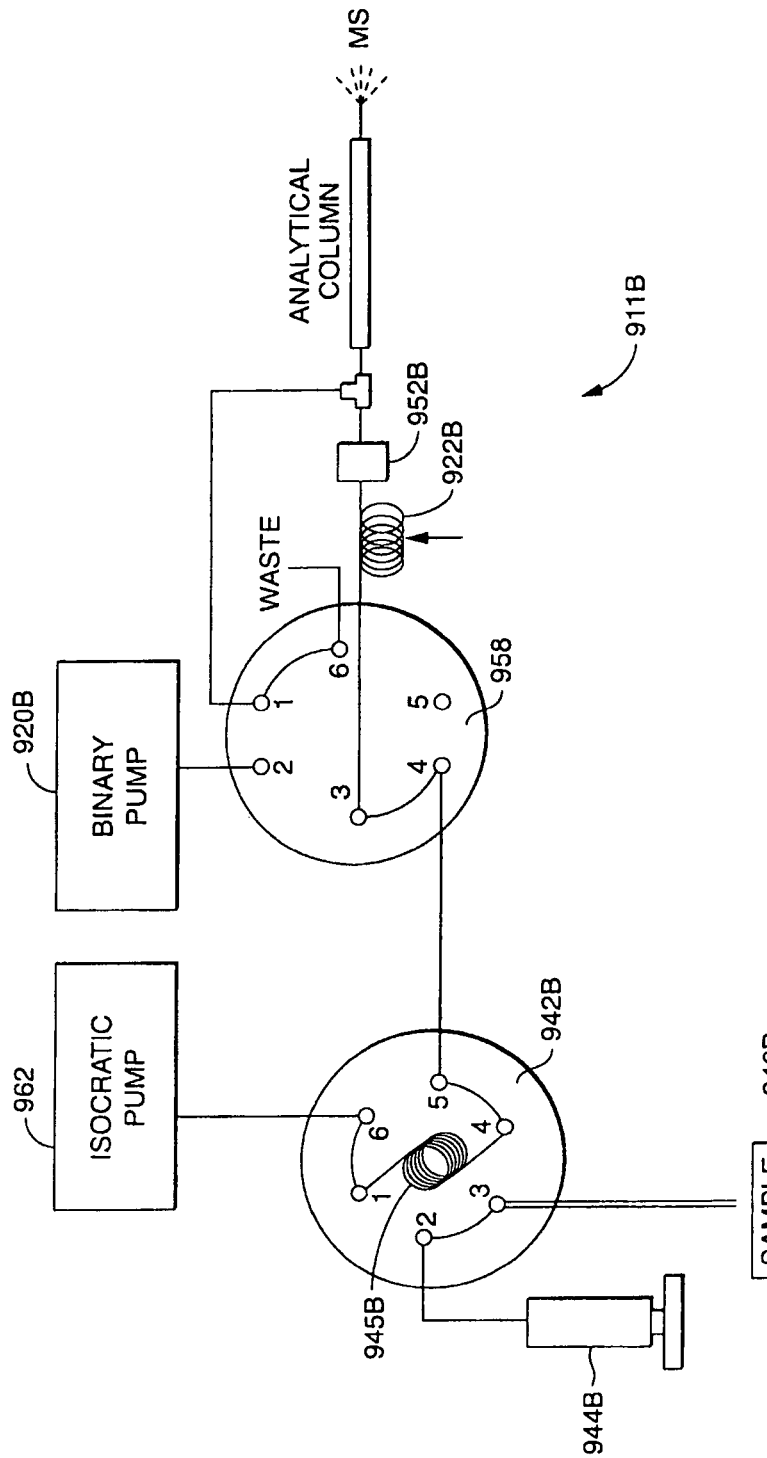
FIG. 19 is a somewhat schematic block diagram illustrating still another LC instrument using a gradient storage device with a vent valve, binary pump and isocratic pump in accordance with the subject technology.

Referring now to FIGS. 17-19, performance of an LC instrument can be further improved by reducing gradient delay time, i.e., the time taken to delivery the gradient, whether or not preformed, from the storage capillary or location to the column. In brief overview, the gradient delay time can be reduced by co-locating or directly connecting the gradient storage device to the column. Further, gradient dispersion is also reduced by the co-location and sample injection time is reduced by using a higher gradient forming flow rate for injection.

Referring to FIG. 17, a somewhat schematic block diagram illustrating a LC instrument using a gradient storage device without a vent valve is referred to generally by the 911. As will be appreciated by those of ordinary skill in the pertinent art, the LC instrument 911 utilizes similar principles to the systems described above. Accordingly, the following discussion is largely directed to the differences. Similar to the systems above, the LC instrument 911 includes an injection valve 942 with a loop 945 for delivering a gradient to the analytical column 967 of a MS detector 969. The injection valve 942 is connected to a binary pump 920, syringe 944 and sample container 946.

A difference of the LC instrument 911 is that a gradient storage device 922 is provided intermediate the injection valve 942 and the analytical column 967. The gradient storage device 922 allows gradient loading at a high flow rate and delivery at a normal flow rate. The backpressure generated when the gradient is loaded can be many times higher than that created when the gradient is run. For example, with an analytical column 967 of 25 um inner diameter by 10 cm in length, packed with 3.5 µm particles, sample loading and gradient pre-formation occurs at 250 nl/min under about 8,000 psi of pressure with the analytical column 967 online to reduce sample loading time. Whereas, gradient delivery occurs at 25 nl/min under about 800 psi of pressure for ultra high sensitivity analysis. Because the gradient is loaded at a high flow rate, the sample can be injected at the same time to effectively reduce runtime (e.g., the sample loading time portion of the runtime).

The gradient storage device 922 may be directly connected to the analytical column 967. By having the gradient storage device 922 closely located to the analytical column 967, the delay in delivering the gradient is minimized and dispersion of the gradient is reduced. The gradient storage device 922 may be as simple as an empty section of capillary tubing with or without any filling matrix. The inner diameter of the gradient storage device 922 may be a similar diameter to that of the analytical column 967 but the volume of the gradient storage device 922 is preferably equal or somewhat greater than the gradient volume. In another embodiment, the gradient storage device 922 is integral with the analytical column 967.

To further shorten the gradient loading time, the total gradient delay volume (i.e., the injection loop volume and the gradient storage device volume) is made equal or slightly greater than the gradient volume. In view of the above advantages, it is envisioned that the subject technology has wide application. For example, it could be advantageously applied in high throughput separations such as the second dimension separation of an offline 2D system or in ultra-sensitive analysis using narrower nano-columns (e.g., 25 um i.d.) to form a gradient at about 300 nl/min and deliver the gradient at about 30 nl/min.

Referring to FIG. 18, a somewhat schematic block diagram illustrating another LC instrument using a gradient storage device with a vent valve is referred to generally by the reference number 911A. To denote that the LC instrument 911A has many of the same components of the instrument 911, the suffix "A" is used to identify like elements whenever possible. The LC instrument 911A is similar to that above but includes a trap column 952A and a vent valve 941A intermediate the gradient storage device 922A and the analytical column 967A. By using a vent valve 941A, the LC instrument 911A is well-suited for use with a trap column 952A. The addition of the vent valve 941A allows operating the LC instrument 911A at a loading pressure lower than the running pressure if desired.

Referring now to FIG. 19, still another LC instrument 911B is shown with another arrangement for allowing operating the LC instrument 911B at a relatively low loading pressure. To denote that the LC instrument 911A has many of the same components of the instruments 911, 911A, the suffix "B" is used to identify like elements whenever possible. The LC instrument 911B includes a T-connection 923 intermediate the trap column 952B and the analytical column 967B. The T-connection 923 extends to a binary pump 920B which can ultimately create a flowpath to waste as shown and described above. In effect, the T-connection 923 performs the same function as the vent valve 941A of FIG. 18. The LC instrument 911B also has an isocratic pump 962 and a trap valve 958 similar to that shown and described above with respect to FIG. 15. As can be seen from these co-location examples, it is also envisioned that the sample is injected simultaneously with loading the gradient using a very high flow rate to reduce the sample loading time.

As would be appreciated by those of ordinary skill in the pertinent art, the subject technology is applicable to use not only as a solvent delivery subsystem in a variety of applications with significant advantages for low flow, high pressure applications but could be advantageously used in many applications. For example, the subject technology is very applicable to systems without a trapping column. The functions of several elements may, in alternative embodiments, be carried out by fewer elements, or a single element. Similarly, in some embodiments, any functional element may perform fewer, or different, operations than those described with respect to the illustrated embodiments. Also, functional elements (e.g., pressure and flow transducers and the like) shown as distinct for purposes of illustration may be incorporated within other functional elements, separated in different hardware or distributed in various ways for a particular implementation. Further, relative size and location are merely somewhat schematic and it is understood that not only the same but many other embodiments could have varying depictions.

While the invention has been described with respect to certain illustrative embodiments, those skilled in the art will readily appreciate that various changes and/or modifications can be made to the invention without departing from the spirit or scope of the invention.

Incorporation by Reference

The contents of all references (including literature references, issued patents, published patent applications, and co-pending patent applications) cited throughout this application are hereby expressly incorporated herein in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A system for providing a gradient to a nano-flow capillary liquid chromatography device, the system comprising:
    an aqueous pump for producing a first output and for delivering the gradient;
    an organic pump for producing a second output mixed with the first output to produce a solution;
    a processing device for controlling the pumps;
    a storage capillary for forming the gradient from a portion of the solution;
    a fitting connected to the storage capillary, wherein the fitting forms a first outlet connected to the nano-flow capillary liquid chromatography device and a second outlet; and
    a valve connected to the second outlet and controlled by the processing device designed to form the gradient in the storage capillary by opening the valve to direct resident fluid to waste while the aqueous and organic pumps run to form the gradient, wherein to deliver the gradient to the nano-flow capillary liquid chromatography device, and closing the valve so that the aqueous pump runs to deliver the gradient and the organic pump is offline.

2. A system as recited in claim 1, further comprising:
    a first inline pressure transducer and a first flow transducer for receiving the first output; and
    a second inline pressure transducer and a second flow transducer for receiving the second output; wherein each transducer is in communication with the processing device to provide closed-loop feedback control.

3. A system as recited in claim 1, wherein the storage capillary is sized to minimize backpressure and dispersion to preserve integrity of the formed gradient.

4. A system as recited in claim 1, further comprising fluid combining fitting for mixing the first and second outputs into one fluid stream.

5. A system as recited in claim 1, wherein the nano-flow capillary liquid chromatography device includes a separations column, an injector for receiving the gradient and directing the gradient to the separations column, and a thermally managed compartment for housing the separations column and the injector, and wherein the storage capillary, the fitting and the valve are co-located in the thermally managed compartment.

6. A system as recited in claim 1, further comprising a transport line that connects the fitting to a sample injector of the nano-flow capillary liquid chromatography device.

7. A system as recited in claim 6, wherein the transport line is a capillary tube.

8. A system as recited in claim 6, wherein the gradient is formed and delivered to flow along a path without changing direction.

9. A system as recited in claim 6, wherein the fitting is a T-shaped fitting arranged so that during delivery, the gradient flows from the inlet to the first outlet without changing direction.

10. A system for providing a gradient to a nano-flow capillary liquid chromatography device, the system comprising:
   an aqueous pump for producing a first output and for delivering the gradient;
   an organic pump for producing a second output mixed with the first output to produce a solution;
   a processing device for controlling the pumps;
   a storage capillary for receiving a gradient formed from both the aqueous and organic pump at low pressure;
   a fitting connected to the storage capillary, wherein the fitting forms a first outlet connected to the nano-flow capillary liquid chromatography device and a second outlet; and
   a valve connected to the second outlet and controlled by the processing device designed to form the gradient in the storage capillary by opening the valve to direct resident fluid to waste while the aqueous and organic pumps run to form the gradient, wherein to deliver the gradient to the nano-flow capillary liquid chromatography device, and closing the valve so that the aqueous pump runs to deliver the gradient at high pressure and the organic pump is not active.

11. A system as recited in claim 10, further comprising:
   a first inline pressure transducer and a first flow transducer for receiving the first output; and
   a second inline pressure transducer and a second flow transducer for receiving the second output; wherein each transducer is in communication with the processing device to provide closed-loop feedback control,
   wherein the storage capillary is sized to minimize backpressure and dispersion to preserve integrity of the gradient.

12. A system as recited in claim 10, further comprising fluid combining fitting for mixing the first and second outputs into one fluid stream.

13. A system as recited in claim 10, wherein the nano-flow capillary liquid chromatography device includes a separations column, an injector for receiving the gradient and directing the gradient to the separations column, and a thermally managed compartment for housing the separations column and the injector, and wherein the storage capillary, the fitting and the valve are co-located in the thermally managed compartment.

14. A system as recited in claim 10, further comprising a transport line that connects the fitting to a sample injector of the nano-flow capillary liquid chromatography device.

15. A system as recited in claim 10, wherein the gradient is formed and delivered to flow along a path in a single direction.

16. A system as recited in claim 10, wherein the fitting is a T-shaped fitting arranged so that during delivery, the gradient flows from the inlet to the first outlet in a straight direction.

* * * * *